US008038025B2

(12) United States Patent
Stark et al.

(10) Patent No.: US 8,038,025 B2
(45) Date of Patent: Oct. 18, 2011

(54) MEDICAL WASTE CONTAINER HINGED LID

(75) Inventors: Kenneth O. Stark, San Marcos, CA (US); Thomas J. Standley, San Diego, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 571 days.

(21) Appl. No.: 12/187,981

(22) Filed: Aug. 7, 2008

(65) Prior Publication Data
US 2010/0032441 A1 Feb. 11, 2010

(51) Int. Cl.
*B65D 51/18* (2006.01)
(52) U.S. Cl. .................................. 220/254.3
(58) Field of Classification Search ............... 220/254.3, 220/254.1, 324, 315, 836, 810, 368, 367.1, 220/908.3, 908.1, 908, 832, 831, 263, 262, 220/260, FOR. 203, FOR. 207, FOR. 192, 220/FOR. 193, FOR. 195; 215/237, 235, 215/280, 273, 200; D34/9, 8, 10, 7; D9/435; 206/364; *B65D 51/18, 50/04, 50/02*
See application file for complete search history.

(56) References Cited

U.S. PATENT DOCUMENTS

| 4,158,902 | A | 6/1979 | Chernack et al. |
| 4,375,849 | A | 3/1983 | Hanifl |
| 4,502,606 | A | 3/1985 | Shillington et al. |
| 4,520,926 | A * | 6/1985 | Nelson ........................ 206/366 |
| 4,600,112 | A | 7/1986 | Shillington et al. |
| 4,746,008 | A * | 5/1988 | Heverly et al. ................. 206/1.5 |
| 4,778,071 | A | 10/1988 | Fillmore |
| 4,816,307 | A | 3/1989 | Honeycutt |
| 4,984,686 | A | 1/1991 | Shillington |
| 5,024,327 | A | 6/1991 | Shillington |
| 5,938,063 | A | 8/1999 | Hoftman |
| 6,062,001 | A | 5/2000 | Kunik |
| 6,092,690 | A | 7/2000 | Bitowft et al. |
| D485,906 | S | 1/2004 | Danssaert et al. |
| 6,986,434 | B1 | 1/2006 | Getsy et al. |
| 6,997,313 | B2 | 2/2006 | Rigling |
| 2004/0163981 | A1* | 8/2004 | Rigling ......................... 206/364 |
| 2006/0070898 | A1 | 4/2006 | Dansaert et al. |
| 2008/0060958 | A1* | 3/2008 | Iske et al. ....................... 206/366 |

FOREIGN PATENT DOCUMENTS

| DE | 197 30 472 C1 | 10/1998 |
| DE | 203 04 131 U1 | 7/2003 |
| EP | 0 891 785 A2 | 1/1999 |
| EP | 1 438 924 A1 | 7/2004 |
| WO | WO 2007065240 A1 * | 6/2007 |

* cited by examiner

*Primary Examiner* — Mickey Yu
*Assistant Examiner* — Robert J Hicks
(74) *Attorney, Agent, or Firm* — Jeanne P. Lukasavage; Diehl Servilla LLC

(57) ABSTRACT

In one aspect, a waste container lid having a closure part and a cap part connected with a hinge, a releasable lock structure and at least one permanent lock structure. In another aspect, a waste container with waste container lid having first closure retention structure and a second closure retention structure that permits the cap to remain opened in a plurality of positions.

28 Claims, 24 Drawing Sheets

MEDICAL WASTE CONTAINER HINGED LID

BACKGROUND OF THE INVENTION

The present invention relates to medical waste disposal containers and lids for such containers, particularly containers for used sharp medical devices, which may require temporary and permanent closure.

The safe and efficient disposal of sharp medical devices such as surgical knives, blades, hypodermic needles and the like is a problem for medical and other healthcare facilities. Disposable containers have been developed in recent years which provide a reasonably high degree of security for disposable sharps articles and materials from hospitals and clinics. Many of these articles, such as needles and surgical blades known as sharps, and other similar articles and materials, must be disposed of in a manner to keep them out of the hands of unauthorized persons and to keep them from being reused.

The containers are normally designed to prevent the removal of materials from the container under ordinary circumstances until permanently closed. The permanent closure is normally present on the container and often used as a temporary cover until the container is filled and ready for permanent closure. However, the permanent closure is frequently unintentionally placed in the permanent position prior to completely filling the container. This results in unnecessary waste of containers and unnecessary cost. Therefore, it is desirable that the container be completely filled prior to permanent closure for disposal.

There is a need for a closure that may be safely used as a temporary closure without the problem of unintentionally placing it in the permanent closure position.

SUMMARY OF THE INVENTION

In a first embodiment, a waste container comprises a base having a bottom wall, a side wall and a top defining a receptacle for receiving sharps, the side wall extending upwardly from the bottom wall, the top connected to an upper portion of the side wall and having an opening therethrough. The container further comprises a lid having a closure part and a cap part having an aperture therethrough, the lid being connectable to the top via the cap part, the lid having a hinge connecting the closure part to the cap part, the hinge allowing the closure part to move between an open position which allows access to the aperture for placing sharps in the receptacle to a closed position covering the aperture. In the first embodiment, a releasable lock structure is provided including a releasable lock detent on one of the cap part or closure part of the lid and a releasable lock projection on the other of the cap part or closure part of the lid, the releasable lock projection adapted to form a connection with the releasable lock detent upon movement of the lid to the closed position, the connection being releasable upon application of force to the releasable lock tab in a direction substantially radial to the lid and allowing the lid to be moved to the open position. The container according to the first embodiment further includes at least one permanent lock structure including a permanent lock tab on one of the closure part or the cap part of the lid and a permanent lock catch on the other of the closure part or the cap part of the lid, the permanent lock tab movable to engage the permanent lock catch when the lid is in the closed position, the permanent lock catch adapted to irreversibly engage the permanent lock tab such that force required to open the permanent lock structure is substantially transverse to the force required to move the closed lid to the open position.

An optional feature of the container according to the first and other embodiments is a skirt portion positioned around a periphery of the closure part of the lid, the skirt portion having two opposed edges substantially aligned with two ramps located on the cap part of the lid with the opposed edges of the skirt portion and disposed on opposite sides of the hinge, the edge portions adapted to cooperate with the ramps to retain the lid in an open position. The ramp can be curved radially inwardly toward the hinge and are inclined upwardly towards the hinge. The edge portions of the skirt are forced apart by interaction with the angled ramps upon closure of the lid, the skirt closing as the edge portions move along the ramps.

The cap part may include radially projecting fins and the closure part includes stops adapted to cooperate with the radially projecting fins to hold the closure part in a fixed position relative to the cap part of the lid.

The closure part of the lid and the cap part of the lid can be held in various open positions. The closure part of the lid can be held relative to the cap part of the lid in a position between 75° and 135°. In one or more embodiments, the closure part and the cap part of the lid can be held in a fixed position between 180° and 270°.

In some embodiments, the releasable lock detent is located on the cap part of the lid and the releasable lock projection is located on the closure part of the lid. This configuration can be reversed so that the releasable lock detent is located on the closure part of the lid and the releasable lock projection is located on the cap part of the lid.

In specific embodiments, the at least one permanent lock structure has the permanent lock catch located on the closure part of the lid and the permanent lock tab located on the cap part of the lid. This orientation may be reversed so that the at least one permanent lock structure has the permanent lock catch located on the cap part of the lid and the permanent lock tab located on the closure part of the lid.

In detailed embodiments, there are two permanent locking structures. In some of these embodiments, the two permanent locking structures are positioned on opposite sides of the releasable lock structure.

The container may have an aperture which includes a plurality of downwardly facing flexible fingers for helping to keep sharps in the receptacle. The cap part of the lid may include at least one elongate port for needle removal, the at least one port being covered by the closure part of the lid when the lid is in the closed position.

An upper portion of the top may include an outwardly curved rim and the cap part of the lid includes a rim around its periphery, the rim of the top and the rim of the cap part are configured to engage each other in an interference fit for connecting the top and the lid. The lid may be held to the top in a snap-fit arrangement achieved by a plurality of inwardly directed projections on the rim of the cap part engaging the rim of the top.

The closure part and cap part of the lid may be configured to form a leak resistant seal when the lid is in the closed position. The leak resistant seal is adapted to prevent fluids from exiting the container without obstruction of optional autoclave vents. A structural bridge on the closure part of the lid may be provided for increasing stiffness of the closure part.

A second aspect of the invention pertains to waste containers comprising a base having a bottom wall, a side wall and a top defining a receptacle for receiving sharps, the side wall extending upwardly from the bottom wall, the top having an aperture therethrough connectable to an upper portion of the side wall, the aperture having an outwardly curved rim. In this aspect, a lid is provided having a closure part and a cap part, the cap part including a rim configured to engage the rim of the receptacle in an interference fit for sealing the lid to the top of the receptacle, the lid having a hinge connecting the closure part to the cap part, the hinge allowing the closure part to move to and from an open position which allows access to the aperture for placing sharps in the receptacle and a closed position covering the aperture and forming a leak resistant seal, the cap part having an aperture therethrough. In the second aspect, the two first closure retention structures are positioned on either side of the hinge on the lid, the first closure retention structures having first projection on the cap part and a skirt portion having opposing edges on the closure part, the first projection being curved inwardly towards the hinge and increasing in height along the curve, the opposing edges of the skirt portion adapted to move along the first projection throughout the movement of the lid from a closed position to an open position. In the second aspect, the first closure retention structures adapted to hold the closure part of the lid in a position between about 75° and about 135° relative to the cap part of the lid. In the second aspect, two second closure retention structures are positioned on either side of the hinge on the lid, the second closure retention structures having projections on the cap part extending radially from the cap part and stops on the closure part of the lid, the detents aligned to interact with the projections on the cap part to hold the closure part of the lid in a position between about 180° and about 270° relative to the cap part of the lid; a releasable lock structure. In the second aspect, the container can include a permanent locking structure.

Optional features include autoclave vents located around the aperture; at least one elongate port for needle removal located adjacent the aperture such that removed needles drop into the receptacle; and a structural bridge on the closure part for increasing stiffness of the closure part.

The permanent lock structure may include a permanent lock tab on one of the cap part of the lid or closure part of the lid and a permanent lock catch on the other of the cap part of the lid or the closure part of the lid. The permanent lock tab of some embodiments has a recess and is movable to engage a projection on the permanent lock catch when the lid is in the closed position, the permanent lock catch adapted to irreversibly engage the permanent lock tab such that the force required to open the permanent locking structure must be applied transversely to the direction that the lid opens.

A third aspect of the invention pertains to a container closure comprising a lid having a closure part and a cap part having an aperture therethrough, the lid being connectable to a container via the cap part, the lid having a hinge connecting the closure part to the cap part, the hinge allowing the closure part to move between an open position which allows access to the aperture for placing sharps in the receptacle to a closed position covering the aperture. The third aspect includes a releasable lock structure including a releasable lock detent on one of the cap part or closure part of the lid and a releasable lock projection on the other of the cap part or closure part of the lid, the releasable lock projection adapted to form a connection with the releasable lock detent upon movement of the lid to the closed position, the connection being releasable upon application of force to the releasable lock tab in a direction substantially radial to the lid and allowing the lid to be moved to the open position. The third aspect includes at least one permanent lock structure including a permanent lock tab on one of the closure part or the cap part of the lid and a permanent lock catch on the other of the closure part or the cap part of the lid, the permanent lock tab movable to engage the permanent lock catch when the lid is in the closed position, the permanent lock catch adapted to irreversibly engage the permanent lock tab such that force required to open the permanent lock structure is substantially transverse to the force required to move the closed lid to the open position.

The various embodiments and aspects of the invention described here can be employed individually or in conjunction.

DETAILED DESCRIPTION

Figure 1A:
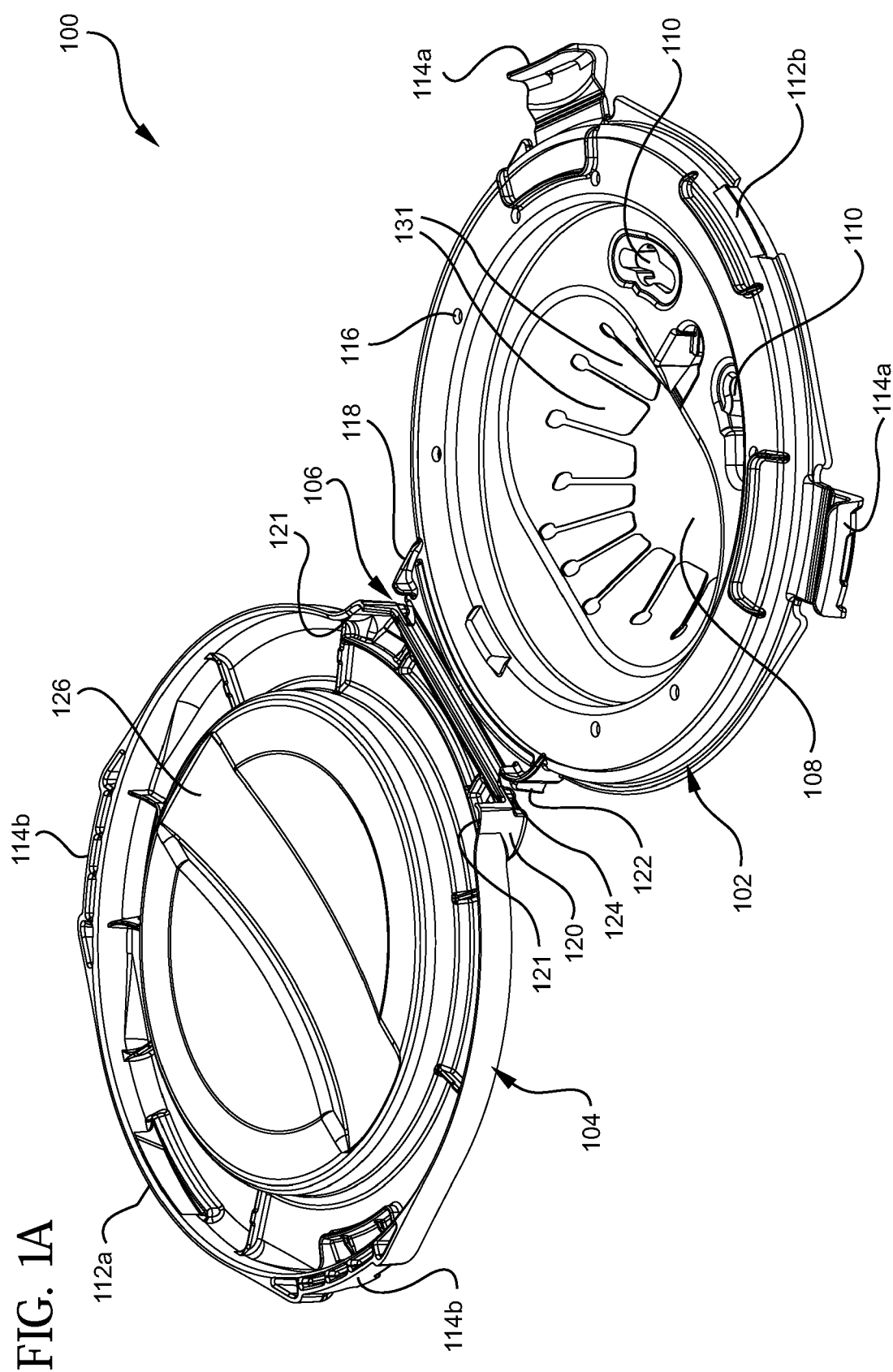
FIG. 1A is a perspective view of a medical waste container hinged lid in a fully open position, showing the top side of the cap part in the foreground and the underside of the closure part in the background.
Figure 1B:
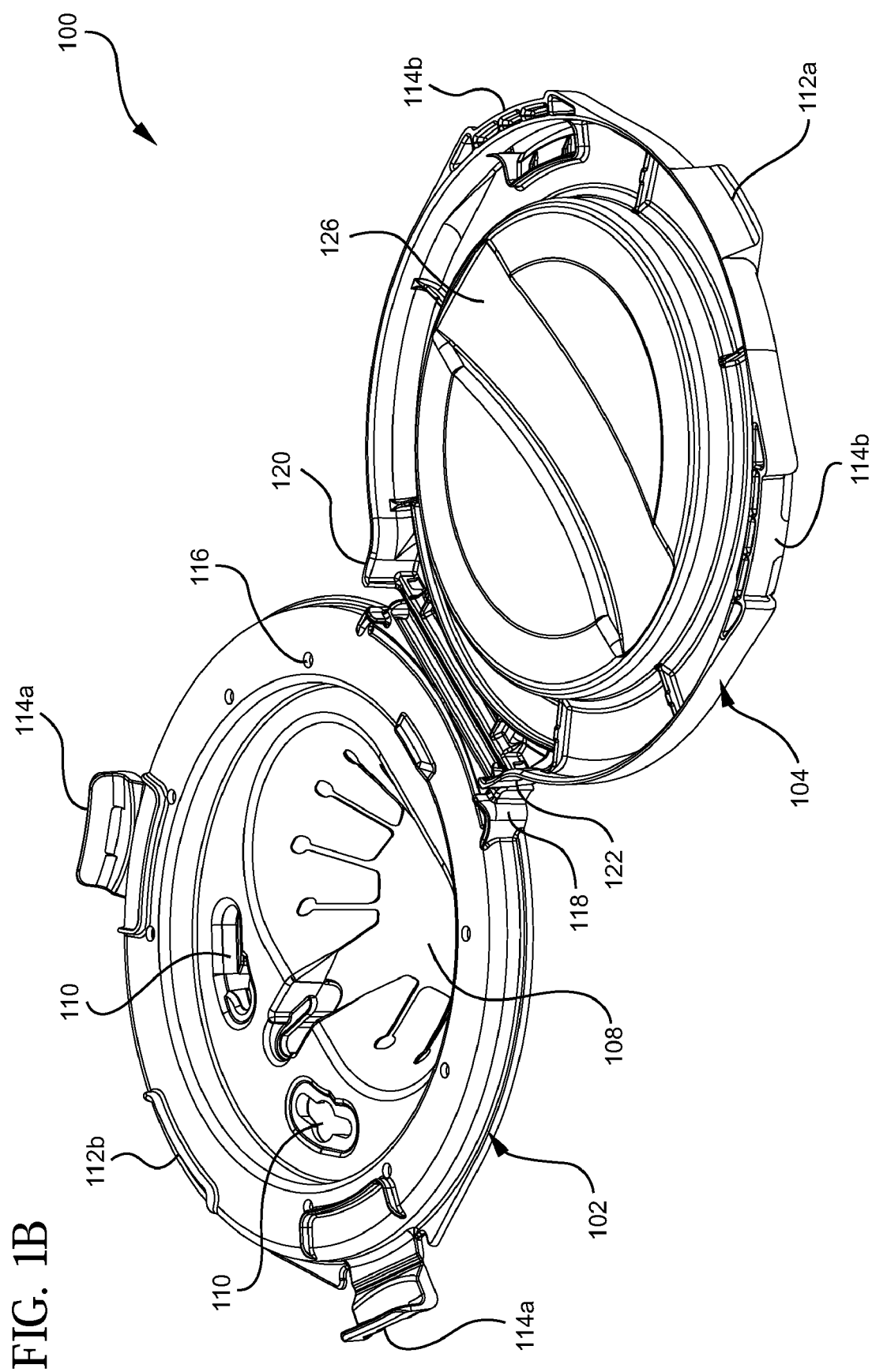
FIG. 1B is a perspective view of a medical waste container hinged lid in a fully open position, showing the top side of the cap part in the background and the underside of the closure part in the foreground.
Figure 1C:
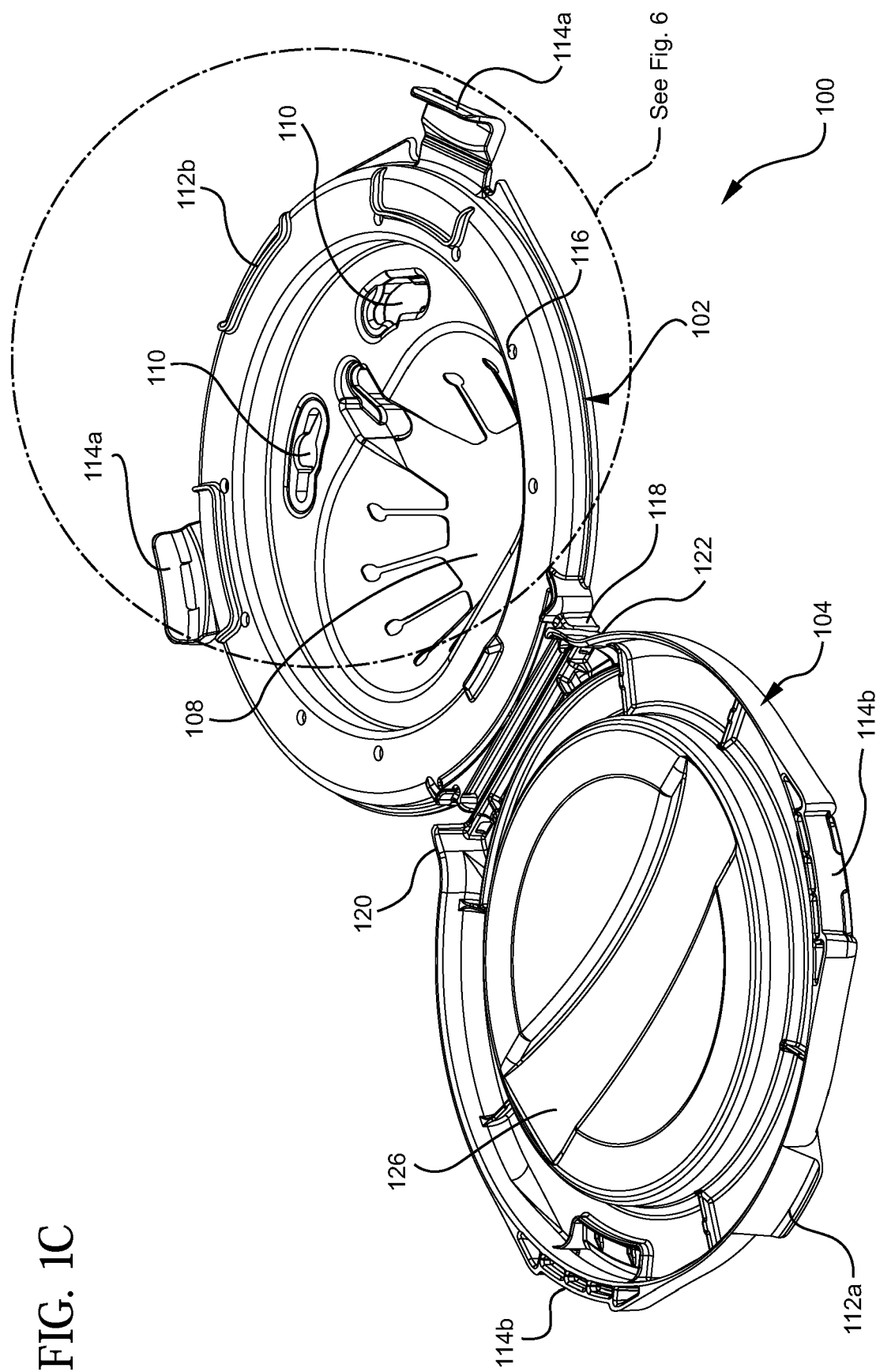
FIG. 1C is a perspective view of a medical waste container hinged lid in a fully open position, showing the top side of the cap part in the background and the underside of the closure part in the foreground.

Before describing several exemplary embodiments of the invention, it is to be understood that the invention is not limited to the details of construction or process steps set forth in the following description. The invention is capable of other embodiments and of being practiced or being carried out in various ways.

As used in this specification and the appended claims, the singular forms "a", "an" and "the" include plural referents unless the context clearly indicates otherwise. Thus, for example, reference to "a cap" includes a combination of two or more caps, and the like. Embodiments of the invention will be described with reference to the drawings. For convenience, the same reference numeral is used to show similar parts on the various drawings.

Figure 1D:
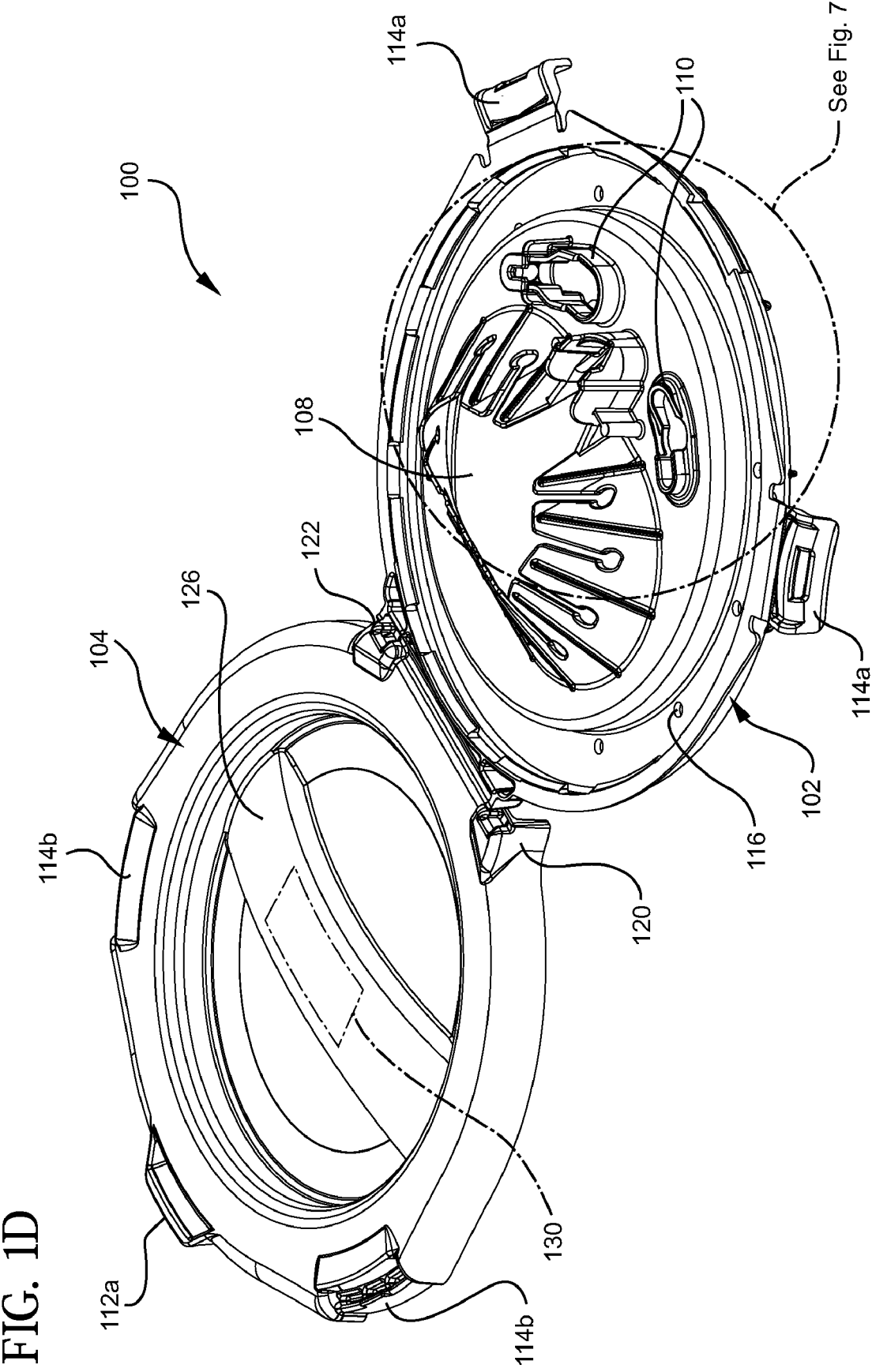
FIG. 1D is a perspective view of a medical waste container hinged lid in a fully open position, showing the top side of the closure part in the background and the underside of the cap part in the foreground.

The present invention pertains to a waste container lid and waste containers including such lids. Referring now to FIGS. 1-7, a first embodiment of a waste container lid 100 is composed of two main parts, a cap part 102 and a closure part 104. The cap part 102 and closure part 104 of the lid 100 are connected by a hinge, which may be in the form of a living hinge 106. FIGS. 1A-1D show various perspective views of a lid 100 in an open position. FIG. 1D shows the lid 100 in an inverted position to show the underside of the cap part 102 and the top side of the closure part 104. The cap part 102 and closure part 104 can be pivoted along the hinge 106 to close the lid 100. FIG. 3 shows the lid 100 in a closed position.

Figure 8:
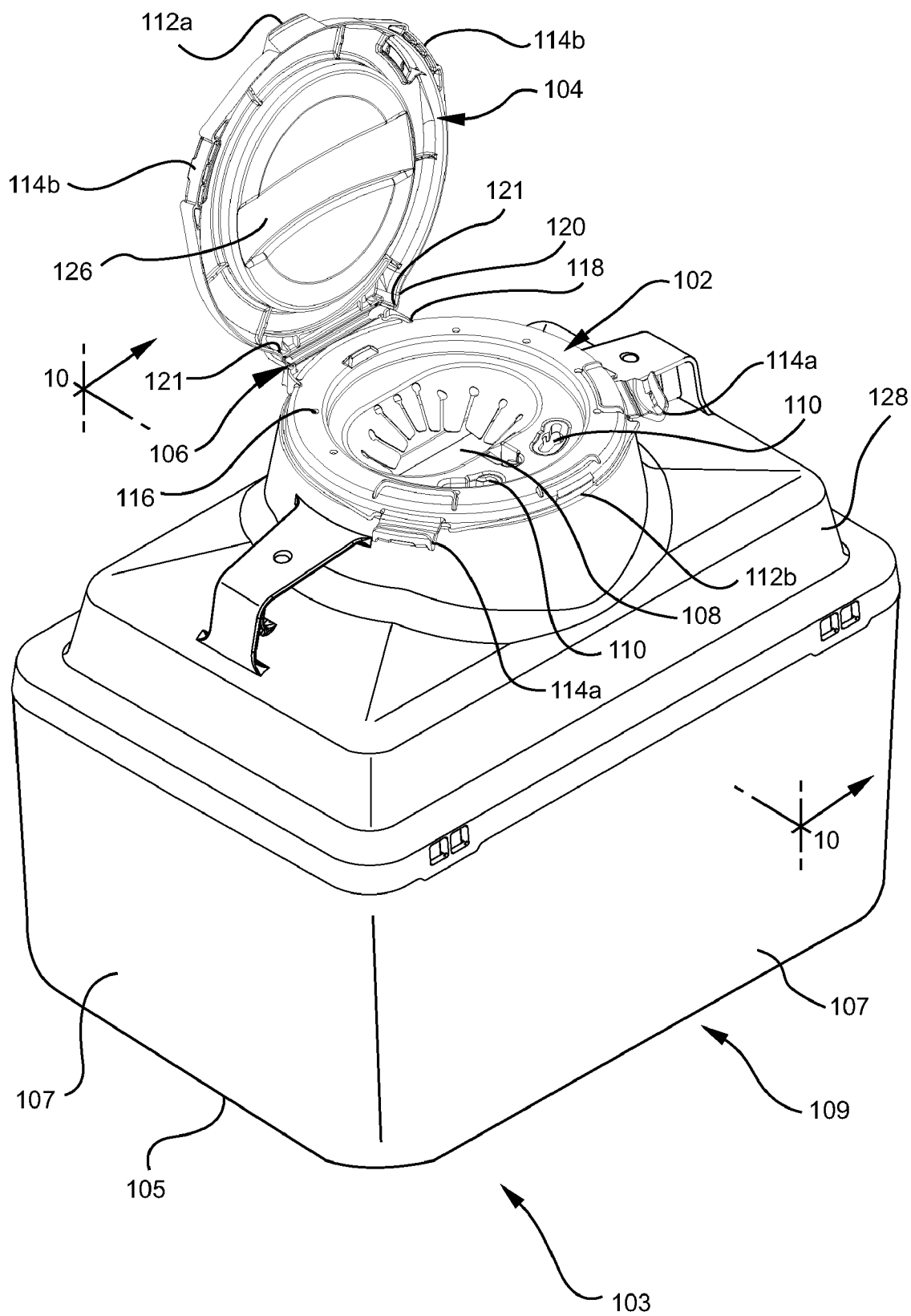
FIG. 8 is a perspective view of a medical waste container lid in an open position on a medical waste container, showing the closure part in an upright position.
Figure 17:
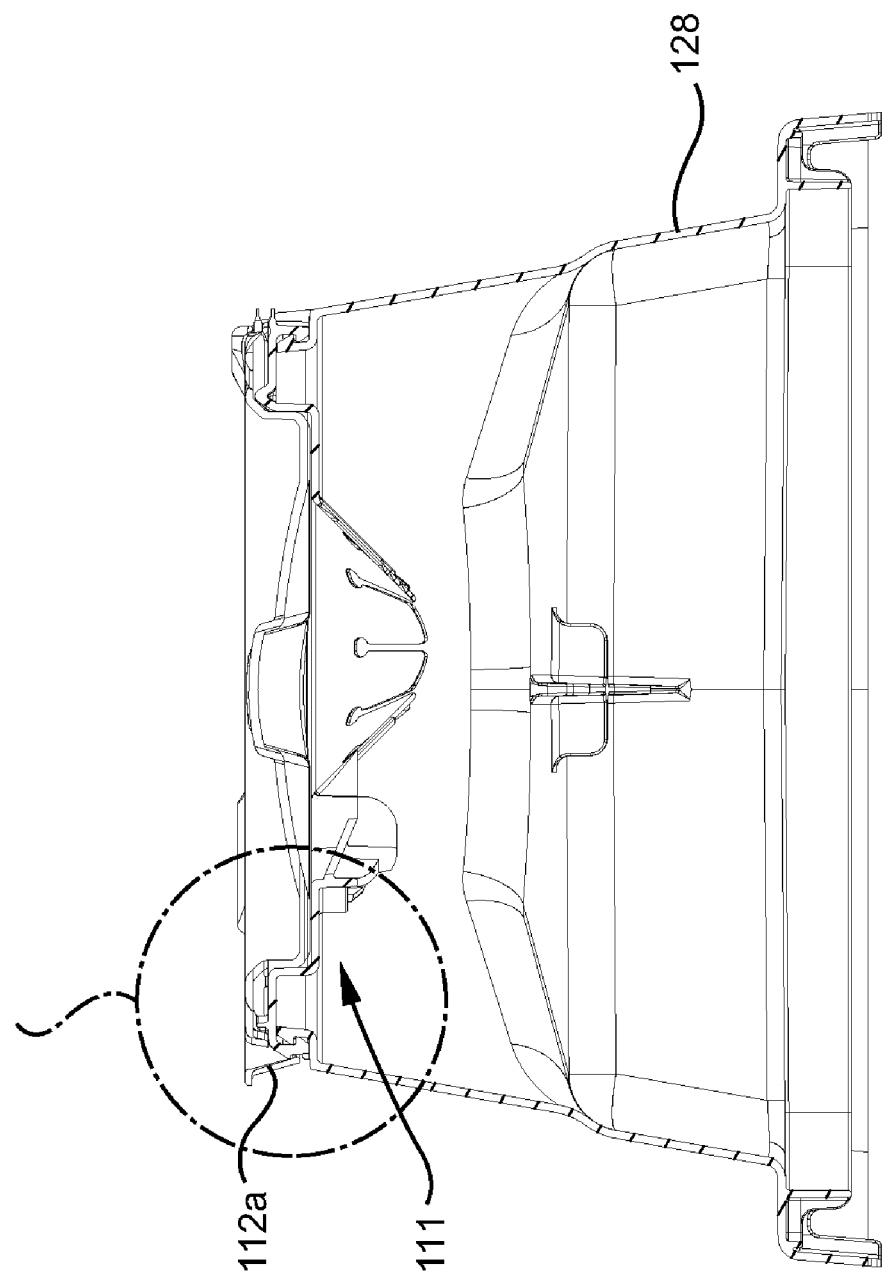
FIG. 17 is a cross-section of the container and the medical waste container lid of FIG. 16 taken along line 17-17.

The cap part 102 includes an aperture 108 which allows waste to pass through the cap part 102 and into a container when the lid is attached to a container. The size and shape of the aperture 108 depends on the desired functionality of the lid 100. For example, the Figures show a lid 100 adapted for use with a sharps container 103, as shown in FIG. 8. The sharps container 103 in FIG. 8 is shown as having a generally rectangular configuration with a bottom wall 105 and a plurality of side walls 107 that extend upwardly from the bottom wall 105. The embodiment shown in FIG. 8 also shows the container as having a bottom container portion 109 and a top container portion 128 as separate parts that can be snapped or otherwise fastened together. The top container portion (or top) 128 includes an opening 111 therethrough (shown in FIG. 17), which is sized and positioned to be coaxial with the aperture 108 in the cap part 102 of the lid 100 to allow waste to be placed in the container. The underside of the cap part 102, shown in the embodiment of FIG. 7, may have a series of upwardly curved clips 115 which can engage a ring on the opening 111 of the top container portion 128. The aperture 108 may be sized with respect to the lid 100 to allow additional optional features, for example, needle removal ports 110 and autoclave holes 116 on the cap part 102. The needle removal ports 110 can be configured in a number of different ways to permit removal of standard luer lock fittings, removal of safety needles and removal of luer slip fittings. It may be desirable to provide all three types of needle removal ports to allow easy removal of needles from a variety of medical devices. It will be understood that the container shown is not limited to the configuration shown in FIG. 8. The container can include a unitary top and bottom portion, and the container can be any suitable shape, such as triangular, square, round, oval or other shapes.

The lid 100 has a releasable lock structure having two parts, a releasable lock projection 112a and a releasable lock detent 112b. The releasable lock projection 112a is adapted to fit into the releasable lock detent 112b. The releasable lock projection 112a is shown as being located on the closure part 104 and the releasable lock detent 112b is shown as located on the cap part 102 of the lid 100. It will be understood that this configuration can be reversed so that lock detent 112b is located on the closure part 104 and the lock projection is on the cap part 102. When the releasable lock projection 112a and releasable lock detent 112b are engaged, an audible click may be heard. The releasable locking structure can be released by applying force to the releasable lock projection 112a or the releasable lock detent 112b.

Figure 13:
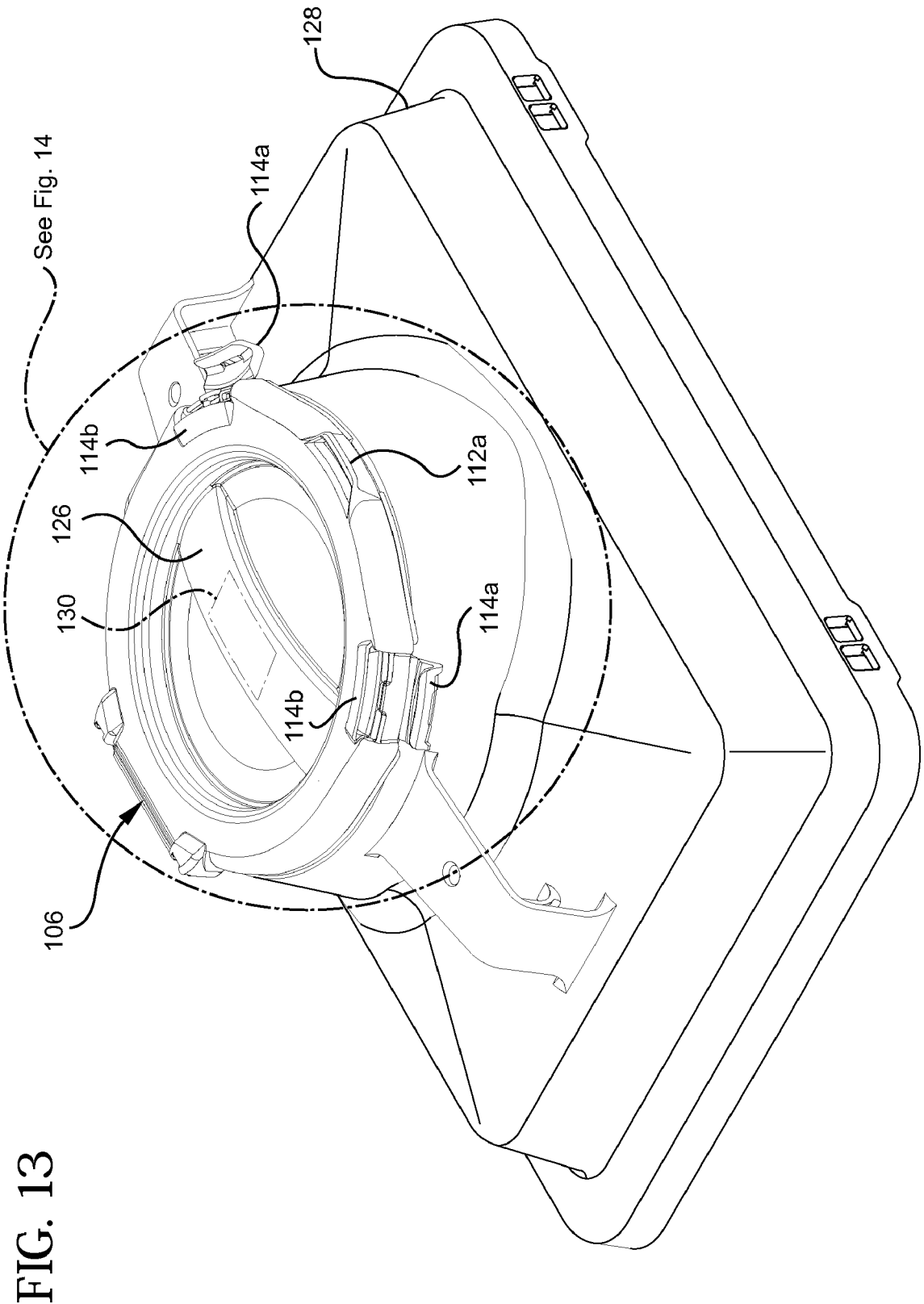
FIG. 13 is a perspective view of the top container portion with the medical waste container lid in the temporarily closed position, showing the top side of the cap part.
Figure 14:
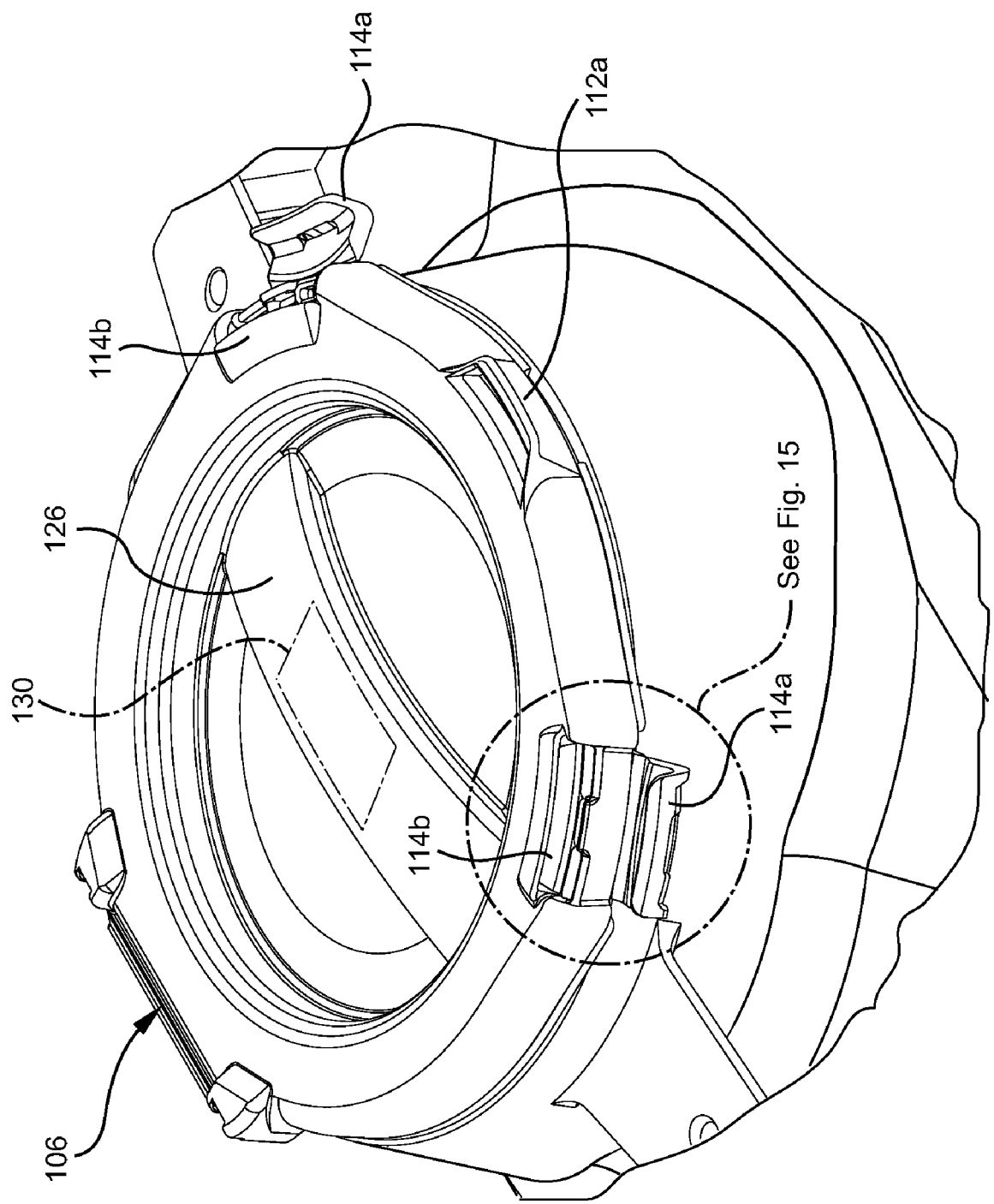
FIG. 14 is an enlarged perspective view of the container and the medical waste container lid in FIG. 13.
Figure 15:
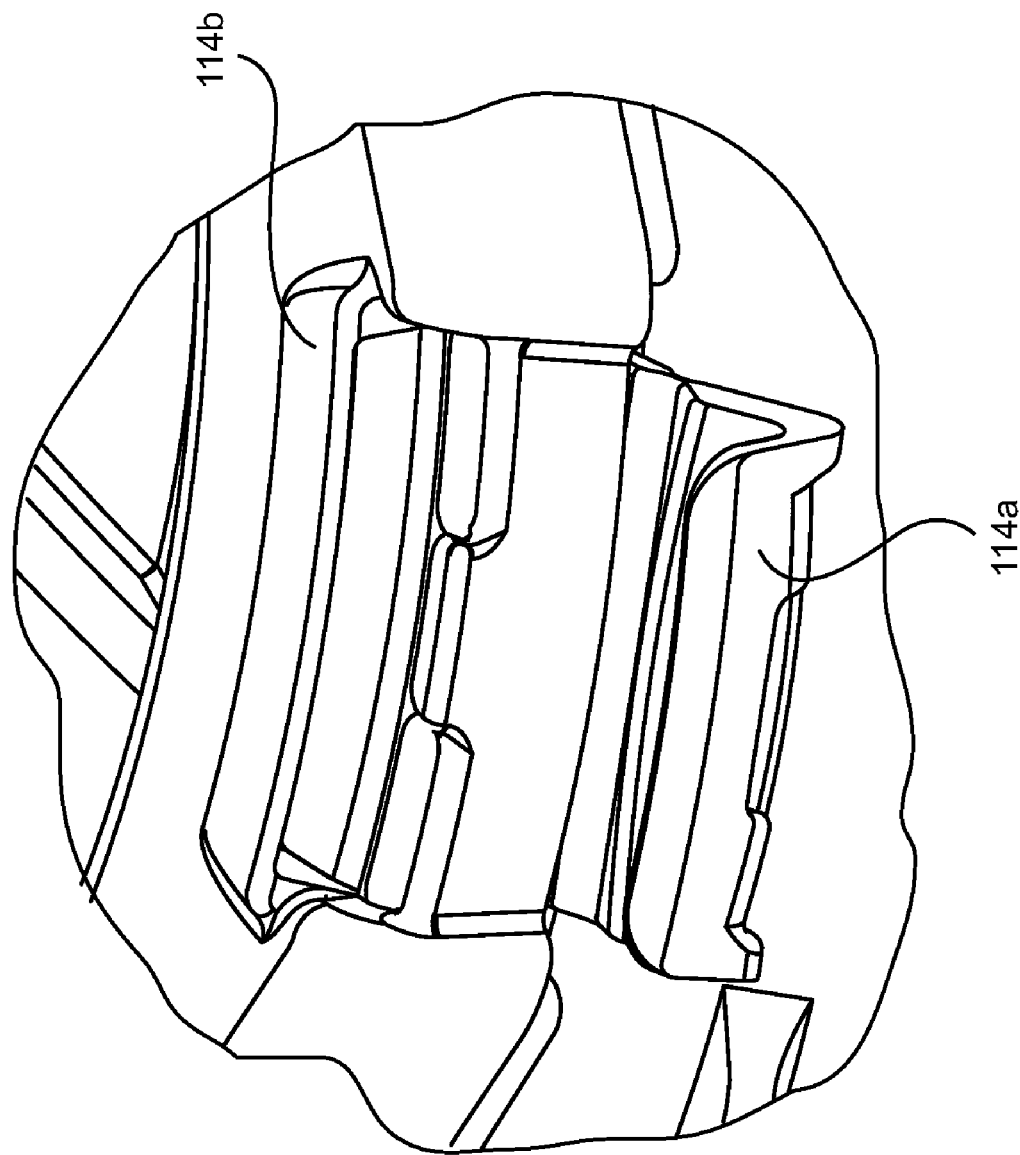
FIG. 15 is enlarged perspective view of the permanent lock structure in an unlocked position from FIG. 14.
Figure 16:
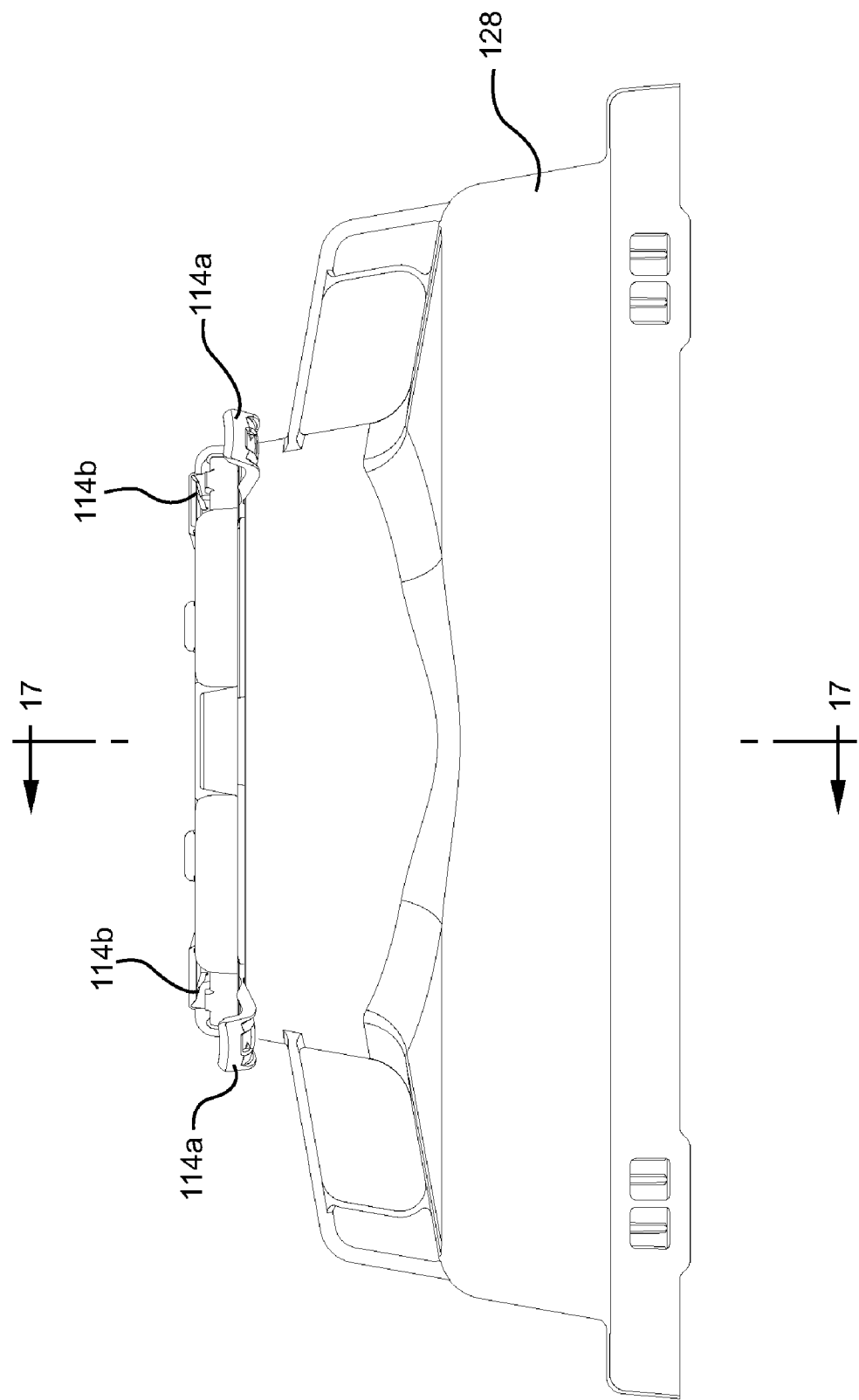
FIG. 16 is a perspective view of a top container portion with the medical waste container lid in the temporarily closed position.
Figure 19:
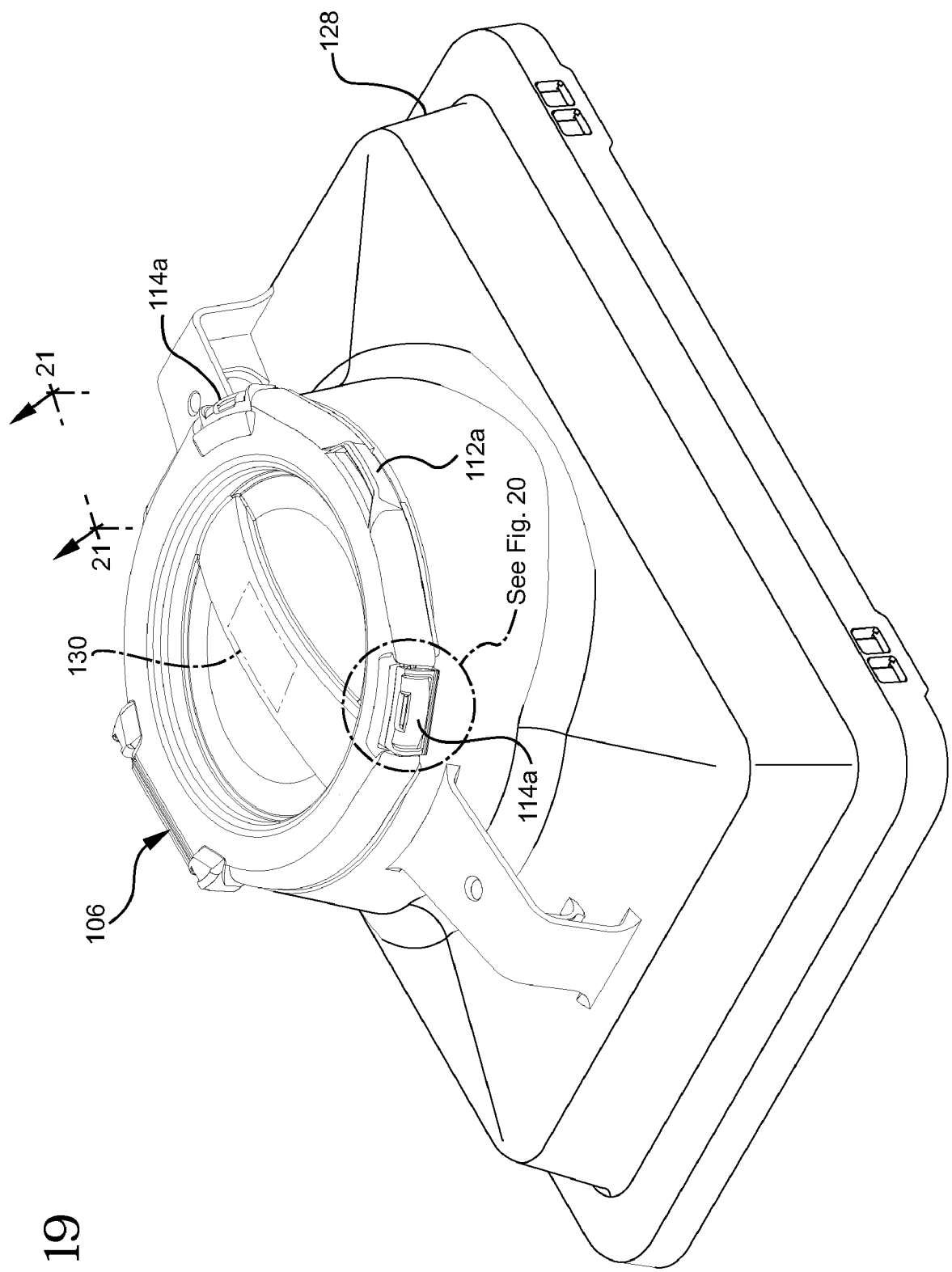
FIG. 19 is a perspective view of a top container portion and the medical waste container lid showing the permanent lock structures engaged.

The lid 100 according to the first aspect can be permanently locked using at least one permanent lock structure including a permanent lock tab 114a and a permanent lock catch 114b which, when engaged, retain the lid 100 in the closed position and prevents unauthorized access to the container when it is ready for disposal with the wasted contained within the container. As used in this specification and the appended claims, a "permanent lock" refers to closure of the lid with a structure that must be opened using either a tool specifically designed for the task or requiring the substantial destruction of the structure to open the cap. In other words, a permanent lock structure is a structure that is intended to lock the container to prevent unauthorized access of the container after it has been locked by a medical practitioner and the container is ready for disposal. In the embodiment shown, two permanent lock tabs 114a are rotated toward the closure part 104 about a living hinge and engaged with the permanent lock catches 114b. FIG. 13 shows the lid 100 on a container portion with the cap in the closed position with the permanent lock structure in the unlocked state. FIG. 19 shows the lid 100 on a container portion with the cap in the closed position and the permanent locks engaged.

Figure 18:
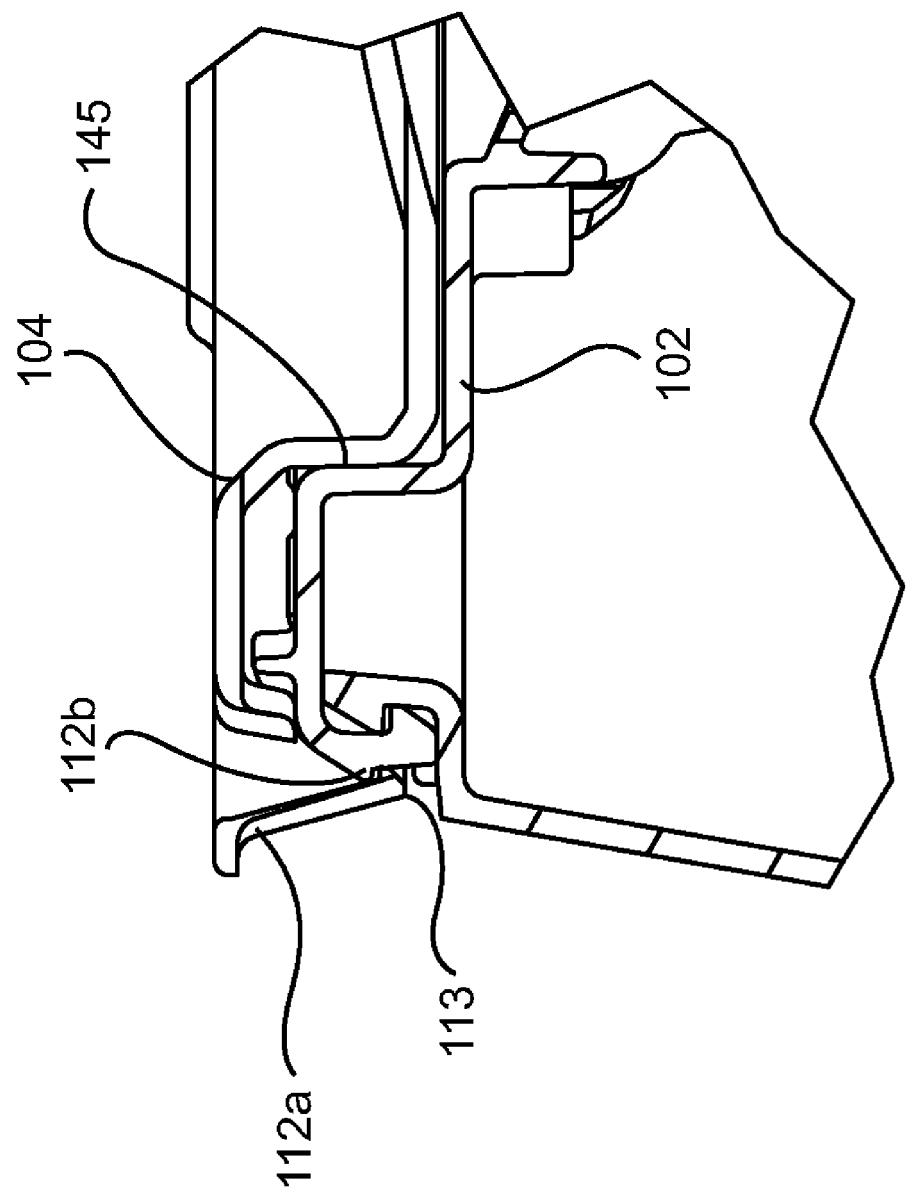
FIG. 18 is a detailed view of the medical waste container lid at the temporary closure taken from FIG. 17.

In use, with respect to FIGS. 1-8 and 13-18, according to a first aspect, the lid 100, when placed on a container, can be temporarily closed by engaging the releasable lock structure by simply closing the closure part 104 on the cap part 102. As best seen in FIG. 18, the releasable lock projection 112a includes an inwardly projecting lip 113 and that cooperates with a releasable lock detent 112b to temporarily close the lid when access to the container is not desired, but when the container is not full and additional waste will be disposed of in the container. For example, it may be desirable to temporarily close the lid to prevent odors from emanating from the container. The releasable lock structure can be disengaged by exerting sufficient radial and/or upwardly directed force on the lock projection 112a to disengage the inwardly projecting lip 113 from the lock detent 112b to rotatably move the closure part about living hinge 106. In other words, the user can unlock the temporary locking structure by grasping the lock projection 112a between the user's thumb and forefinger and pressing radially inwardly with the thumb against the projection 112a and lifting upwardly at the same time to disengage the inwardly projecting lip 113 from the lock detent 112b and rotating the closure part about the hinge 106.

Figure 20:
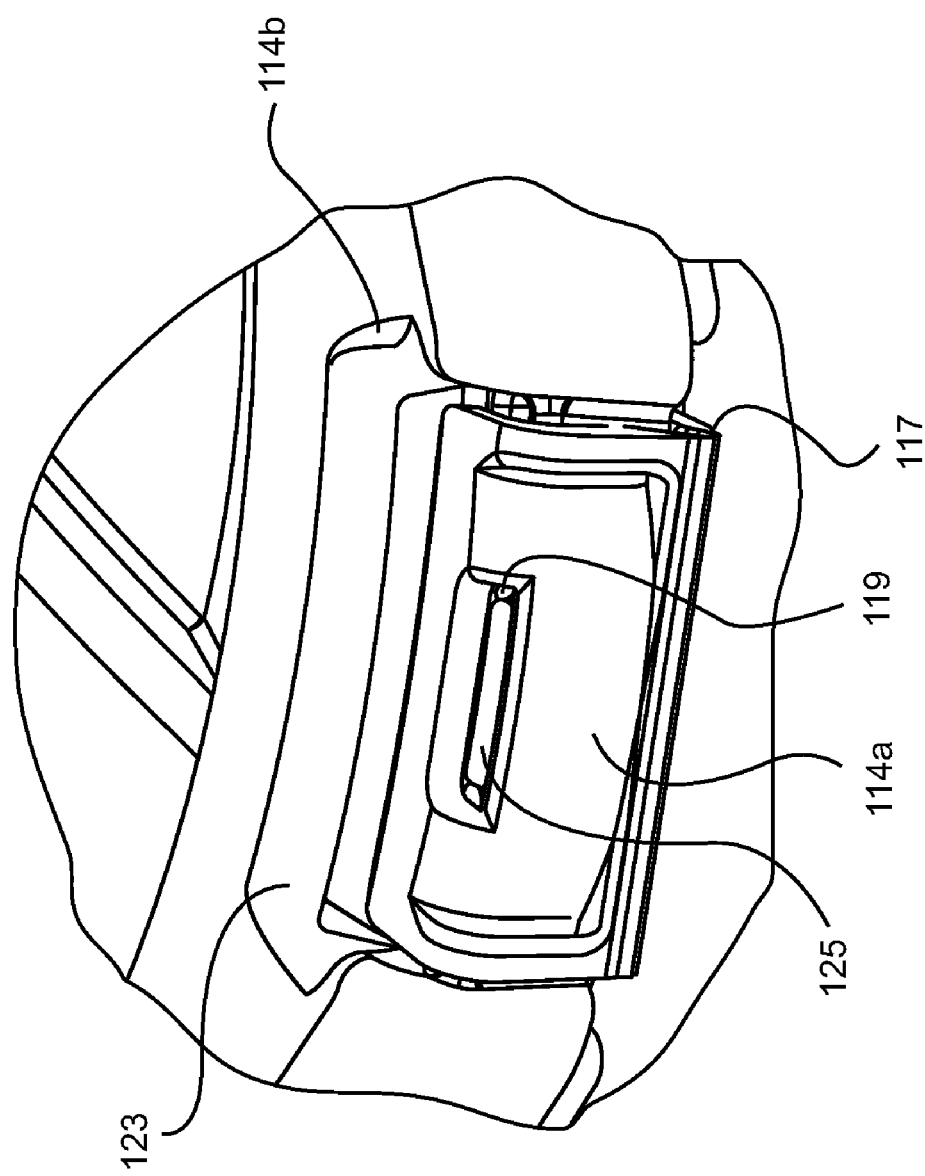
FIG. 20 is a detailed view of the medical waste container lid at the permanent closure taken from FIG. 19.
Figure 21:
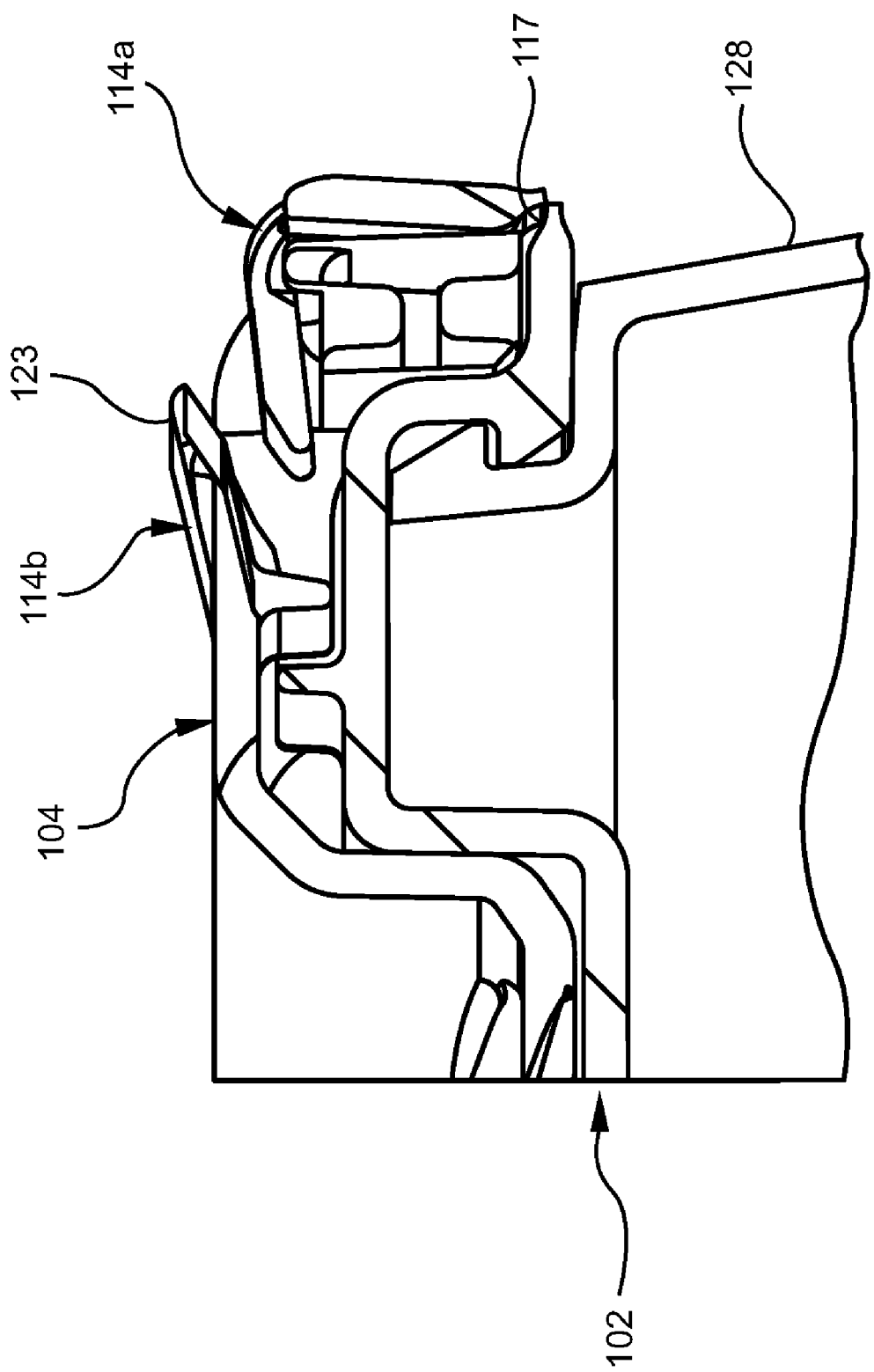
FIG. 21 is a cross-sectional view of the medical waste container lid taken along line 21-21 of FIG. 19.

To permanently lock the lid 100, the lid is placed in the closed position as shown in FIGS. 13-17 by rotating the closure part 104 about the living hinge 106 to close the closure part over the aperture 108, covering the aperture and engaging the releasable lock structure as described above. Until the lid is ready for permanent closure to prevent unauthorized access, the permanent lock tab 114*a* and the permanent lock catch 114*b* are not engaged with each other. Thus, as shown in FIGS. 13-17 the permanent lock tab 114*a* is left in an outwardly extended position, allowing the container to be reopened if desired. The disengaged permanent lock tabs 114*a*, which protrude outwardly when the lid is not permanently locked also provide a visual indication that the container may still be used and is not ready for disposal. The lid is permanently locked when the permanent lock tabs 114*a* are placed in the position shown in FIGS. 19-21. The permanent lock tab 114*a* is engaged with the permanent lock catch 114*b* by rotating the permanent lock tab 114*a* about tab hinge 117. The tab hinge 117 may be a living hinge or any other suitable hinge mechanism. The permanent lock tab 114*a* include a slot 119 that cooperates with a lock catch projection 125 that is part of the permanent lock catch 114*b*. The permanent lock catch 114*b* also includes an overhang 123, which may be inclined upwardly. The overhang 123 prevents easy access to the lock tab 114*a* and thereby prevents unauthorized access to the container once the permanent lock tab 114*a* and permanent lock catch 114*b* have been engaged with each other. As discussed above, "permanent" means that unauthorized access to the container is substantially prevented. It will be appreciated, of course, that access to the contents of the container may be had by destroying a portion of the container or using a tool to pry apart or otherwise alter the permanent lock structure. In addition, the permanent lock structure described herein provides visual, audible and tactile indication to the practitioner that permanent closure of the lid has been achieved when the permanent lock tab 114*a* and lock catch 114*b* snap together. Furthermore, the force holding the lock tab 114*a* and lock catch 114*b* is substantially transverse to the force required to open the container. In other words, if an individual attempted to open the container after engagement of the lock tab 114*a* and the lock catch 114b, the force required to open the container would be substantially upward from the bottom of the container. The force holding the lock tab 114*a* and the lock catch 114*b* are substantially transverse or perpendicular to the direction of the opening force in that the lock tab 114*a* and the lock catch 114*b* would have to be disengaged by moving the lock tab 114*a* radially outwardly from the lid.

Figure 2:
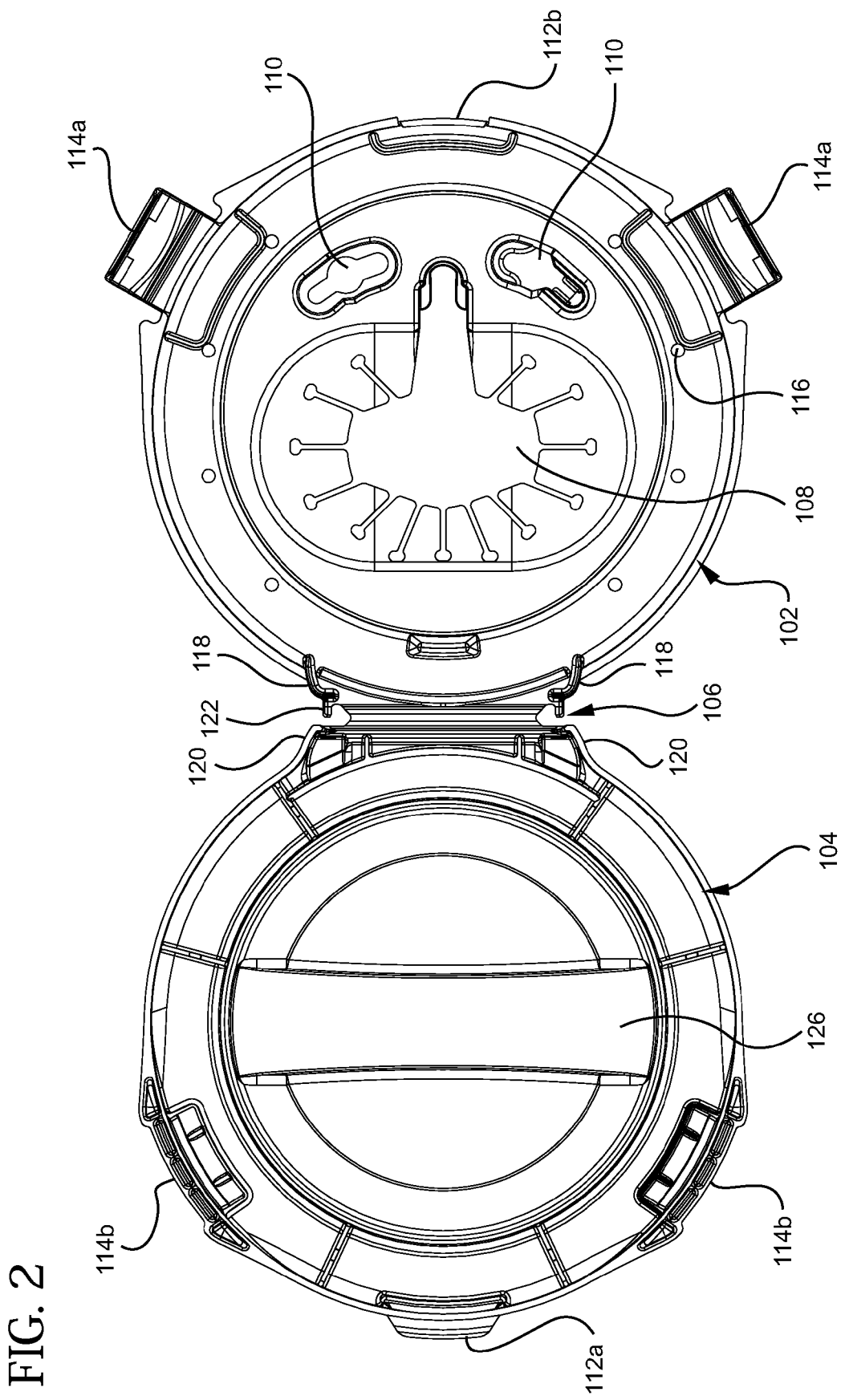
FIG. 2 is a top perspective view of a medical waste container hinged lid in a fully open position, showing the underside of the closure part on the left and the top side of the cap part on the right.
Figure 3:
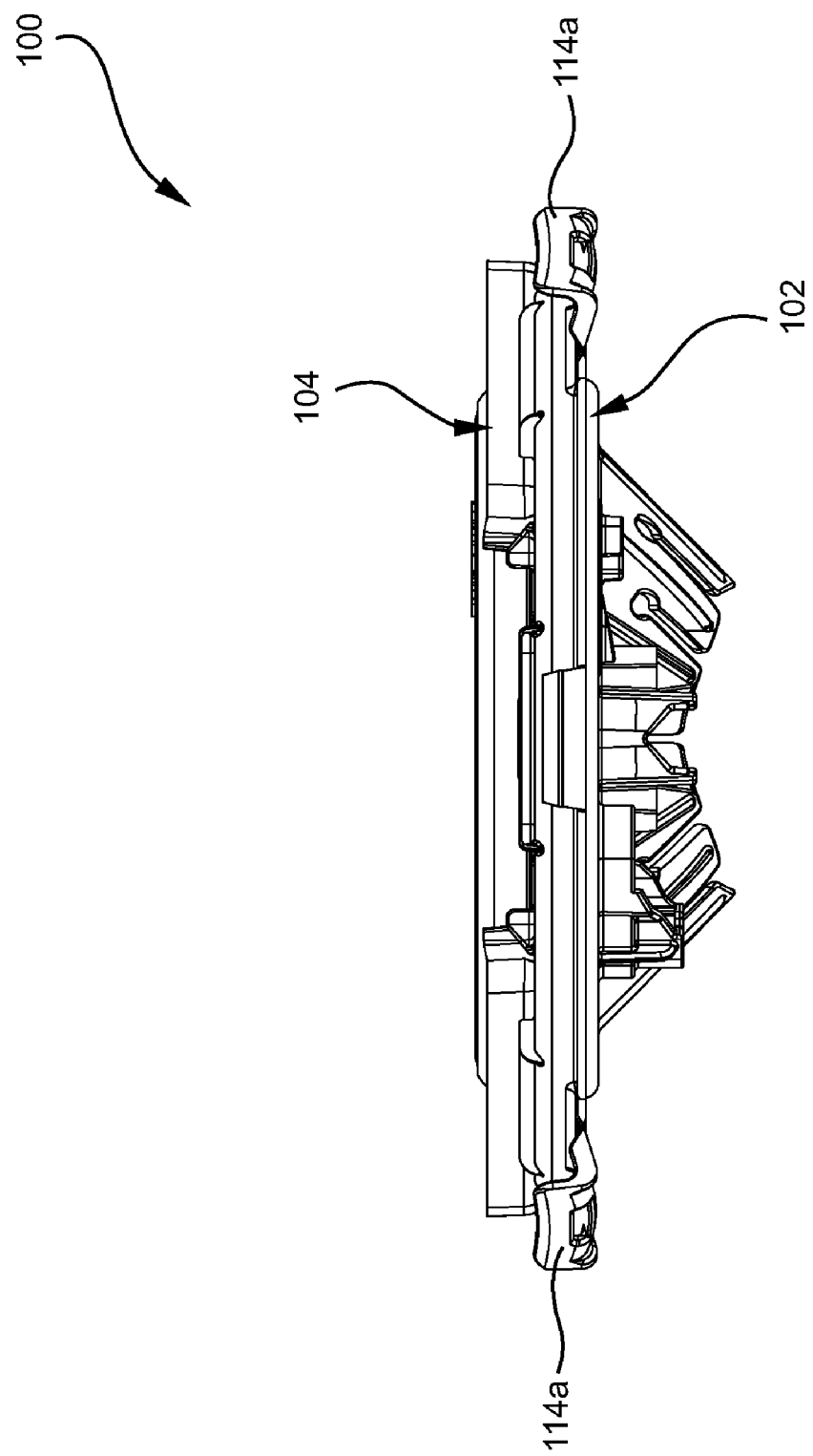
FIG. 3 is a side elevation view of a medical waste container hinged lid in the closed position.
Figure 4:
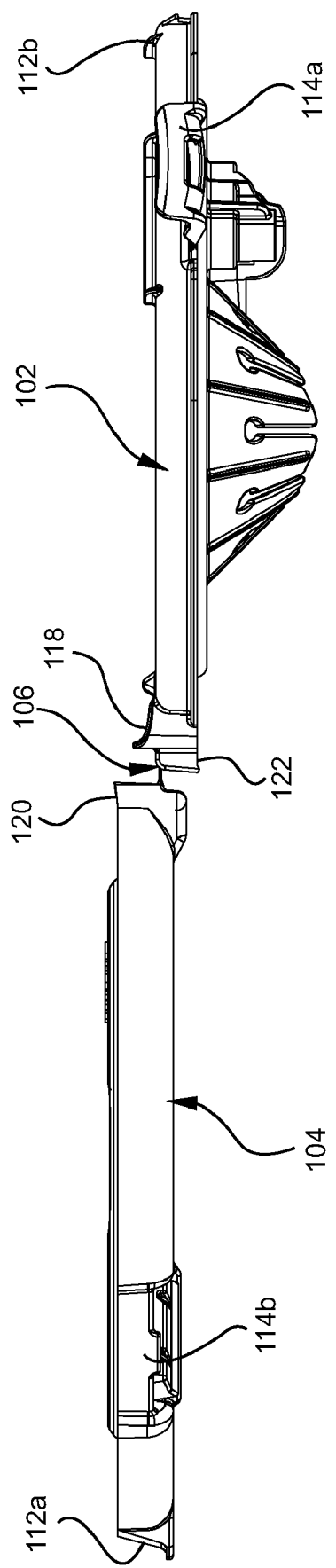
FIG. 4 is a side elevation view of a medical waste container lid in the fully open position showing the closure part on the left and cap part on the right.
Figure 5:
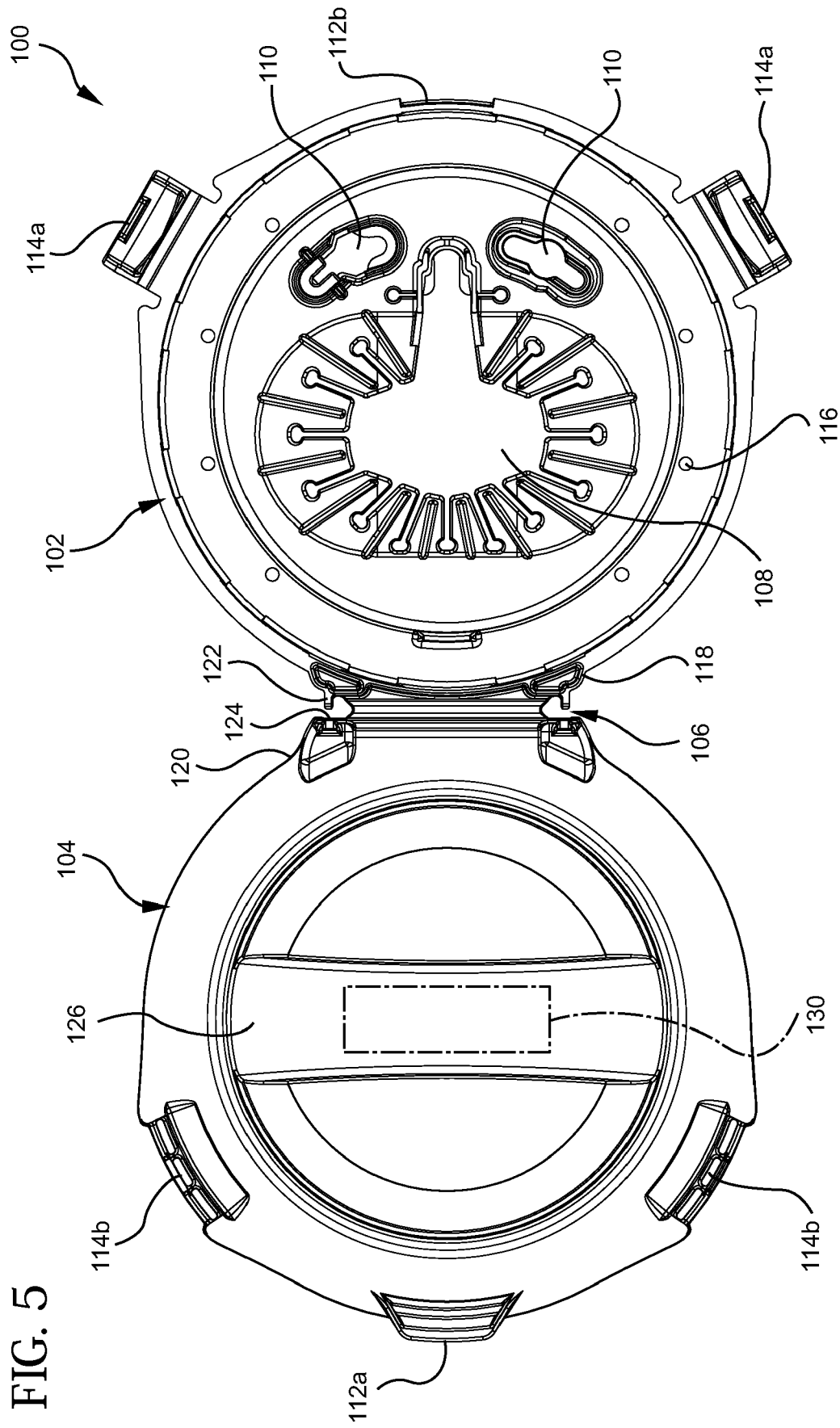
FIG. 5 is a top perspective view of a medical waste container lid in a fully open position, showing the underside of the cap part on the right and the top side of the closure part on the left.
Figure 6:
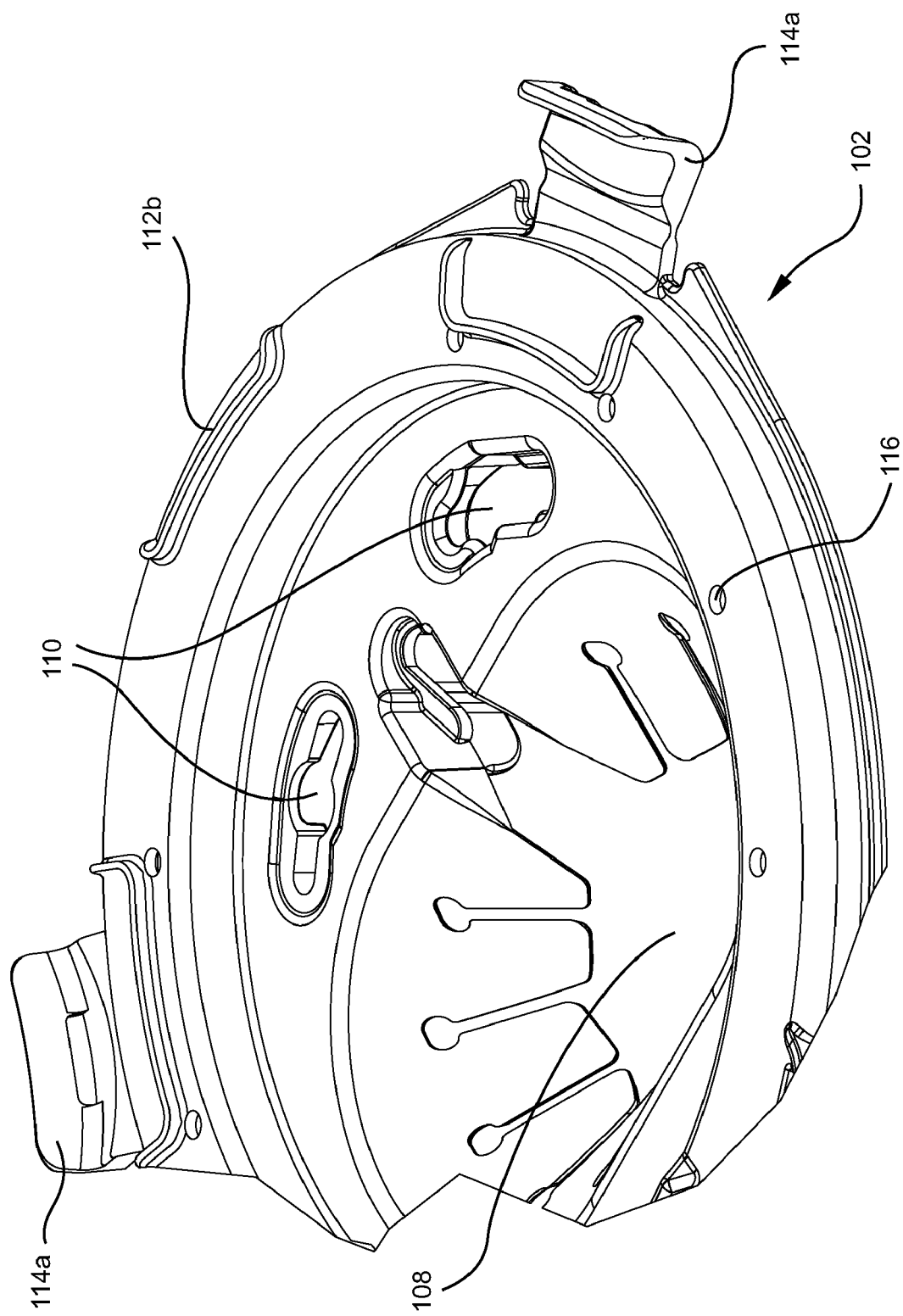
FIG. 6 is an enlarged view of the area of the cap part taken from FIG. 1C as seen from above the cap part.
Figure 7:
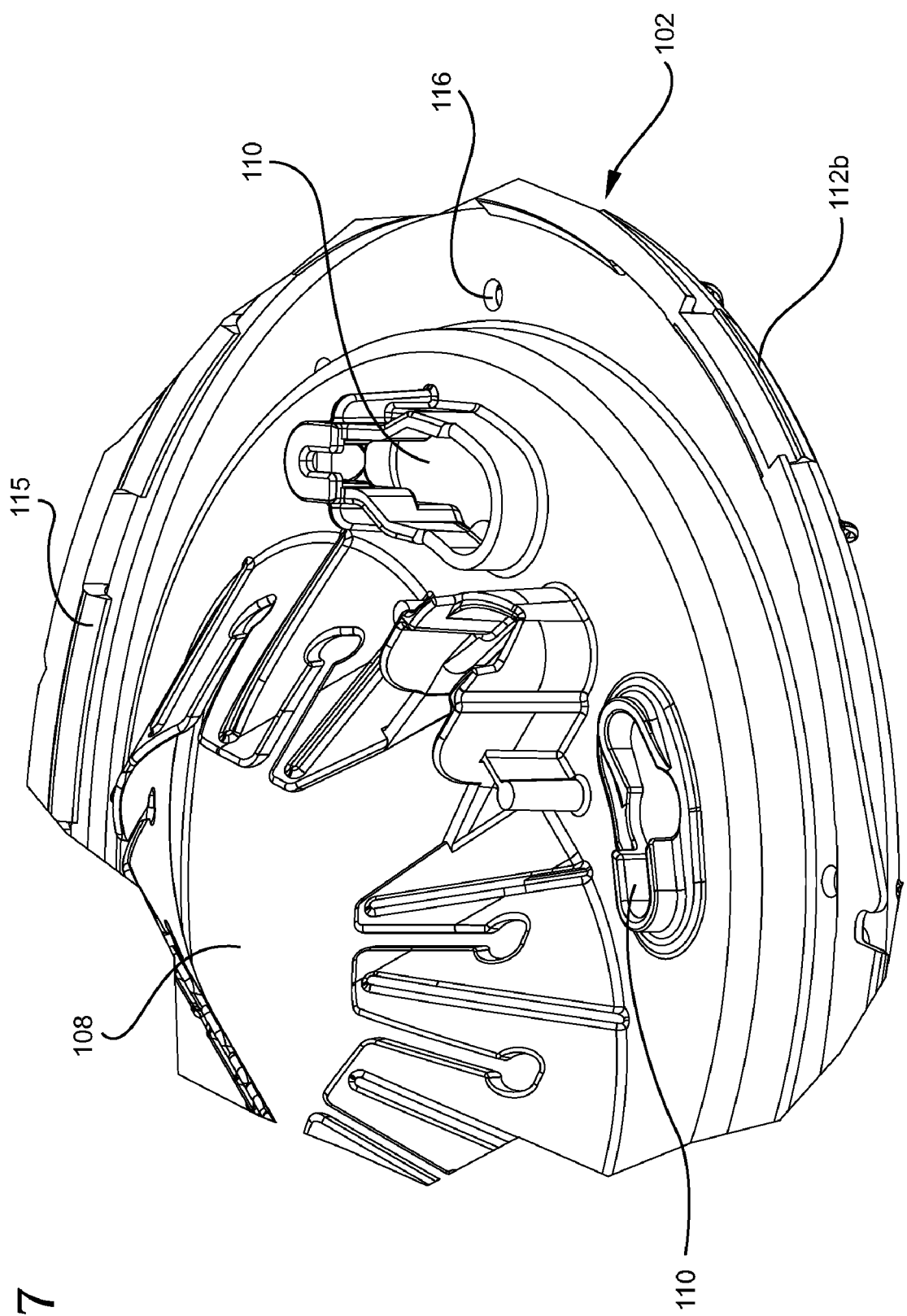
FIG. 7 is an enlarged view of the cap part taken from FIG. 1D as seen from below the cap part.
Figure 9:
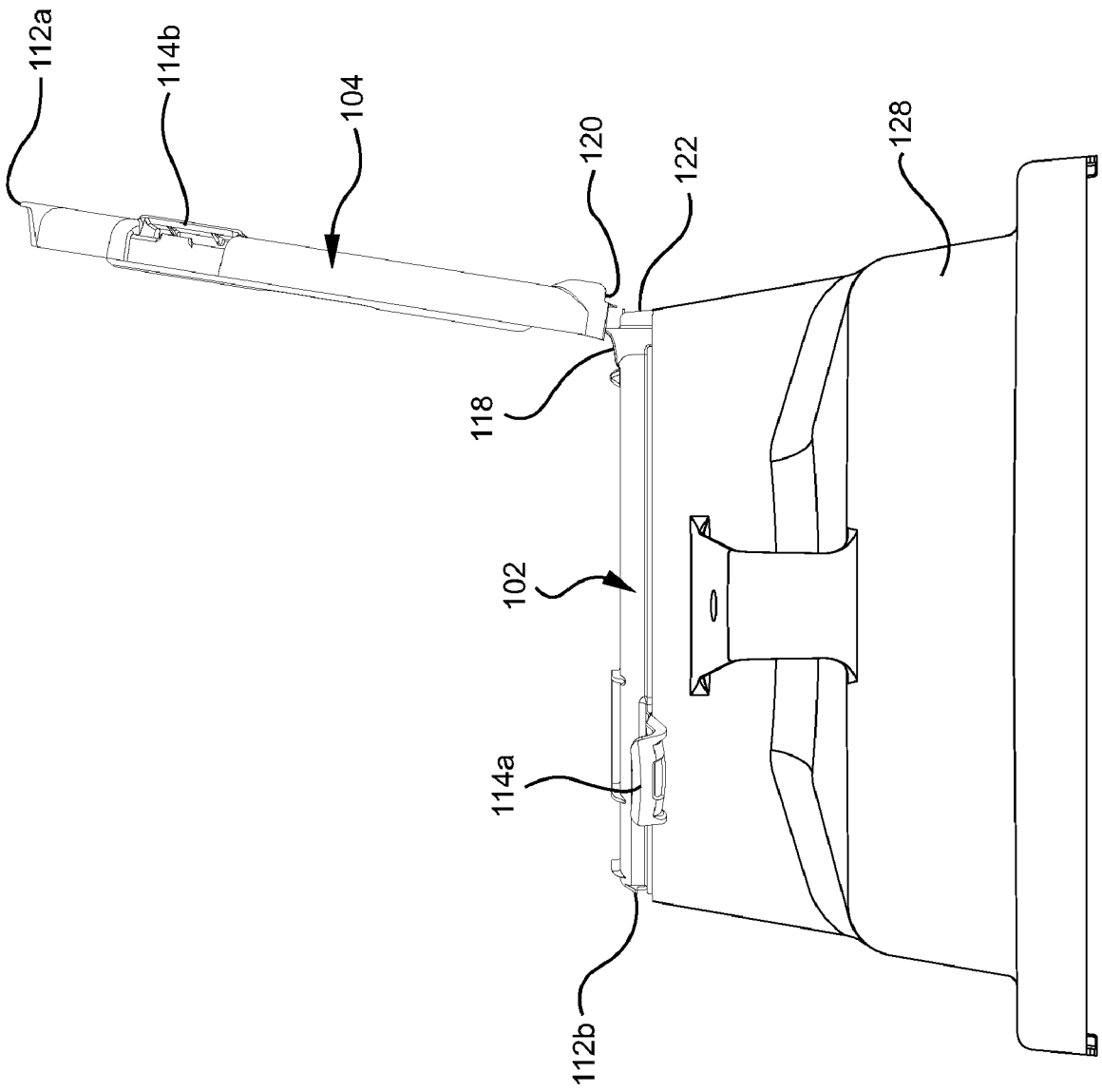
FIG. 9 is a side view of the top container portion and medical waste container lid of FIG. 8, showing the closure part standing in an upright position.

In a second aspect of the invention, shown with respect to FIGS. 2, 4 and 8-13, the lid 100 can be fixed in a plurality of open positions using different closure retention structures. The lid 100 can be fixed in an open position as shown in FIG. 9 with the closure part 104 held at an angle in the range of about 75° and 135° relative to the cap part 102. As best seen in FIG. 2, 4, and 9, the embodiments shown have a projection in the form of a pair of ramps 118 located on the cap part 102 and a skirt 120 located on the closure part 104. The ramps 118 project toward and curve inwardly toward the hinge 106. In addition, ramps are inclined upwardly away from the surface of the cap part 102 and towards the hinge 106. Thus, the ramps increase in height along the curve moving towards the living hinge. The skirt 120 has opposing edges 121 defining a gap, and the edges 121 are spaced apart so that they are adapted to ride along the ramps 118 during the opening/closing of the lid 100. At about the angle that the cap is fixed open in the range of about 75 ° and 135 ° to the cap part, the skirt edges sit upon the ramps 118, keeping the lid in an open position. This first closure retention structure is useful for situations in which the waste container is mounted on a wall or a cart. Application of a downward force to the closure part 104 will cause the skirt edges 121 to spread apart during closing of the lid 100.

Figure 10:
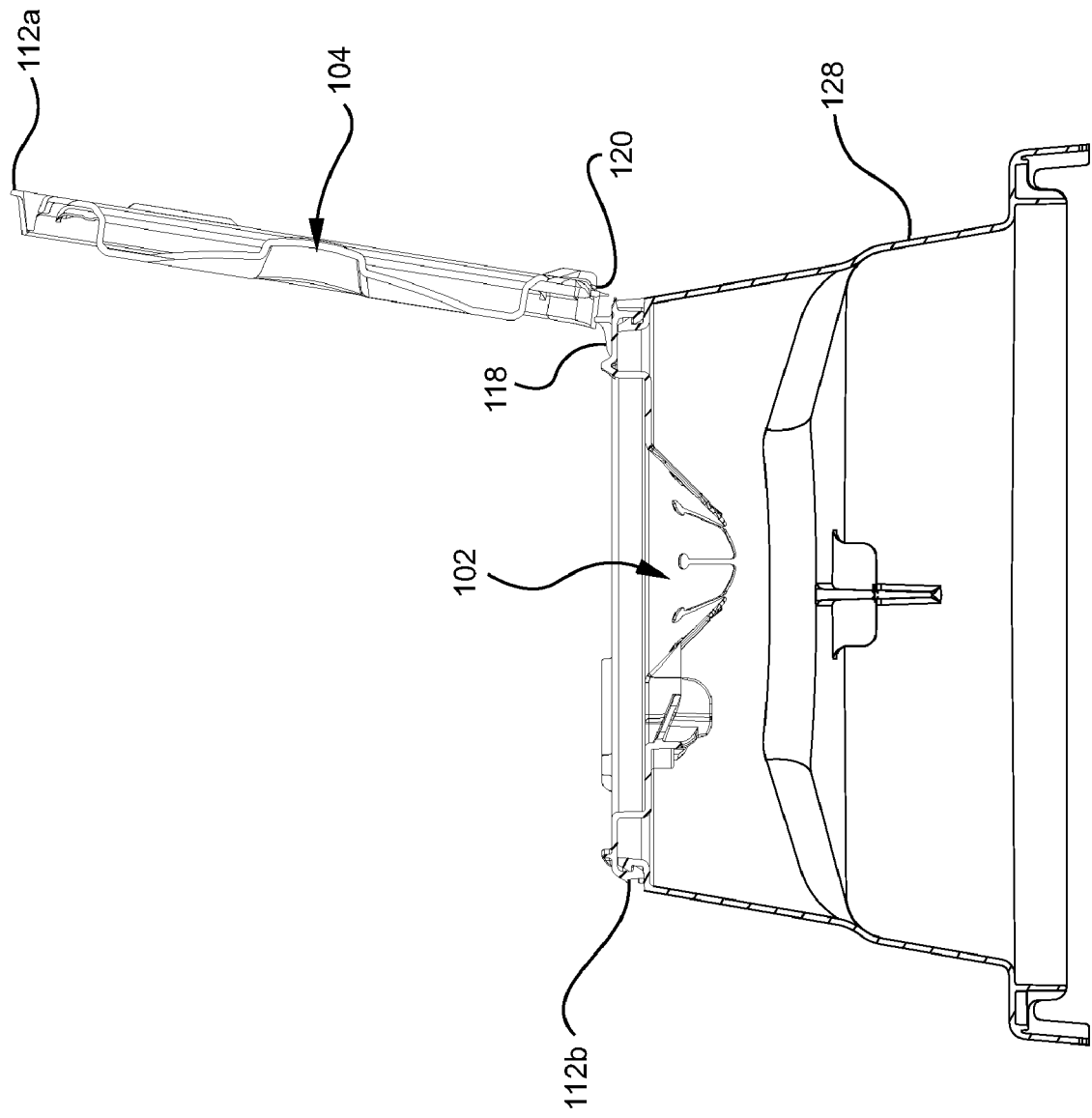
FIG. 10 is a cross section of the top container portion and the medical waste container lid of FIG. 8 taken along line 10-10.
Figure 11:
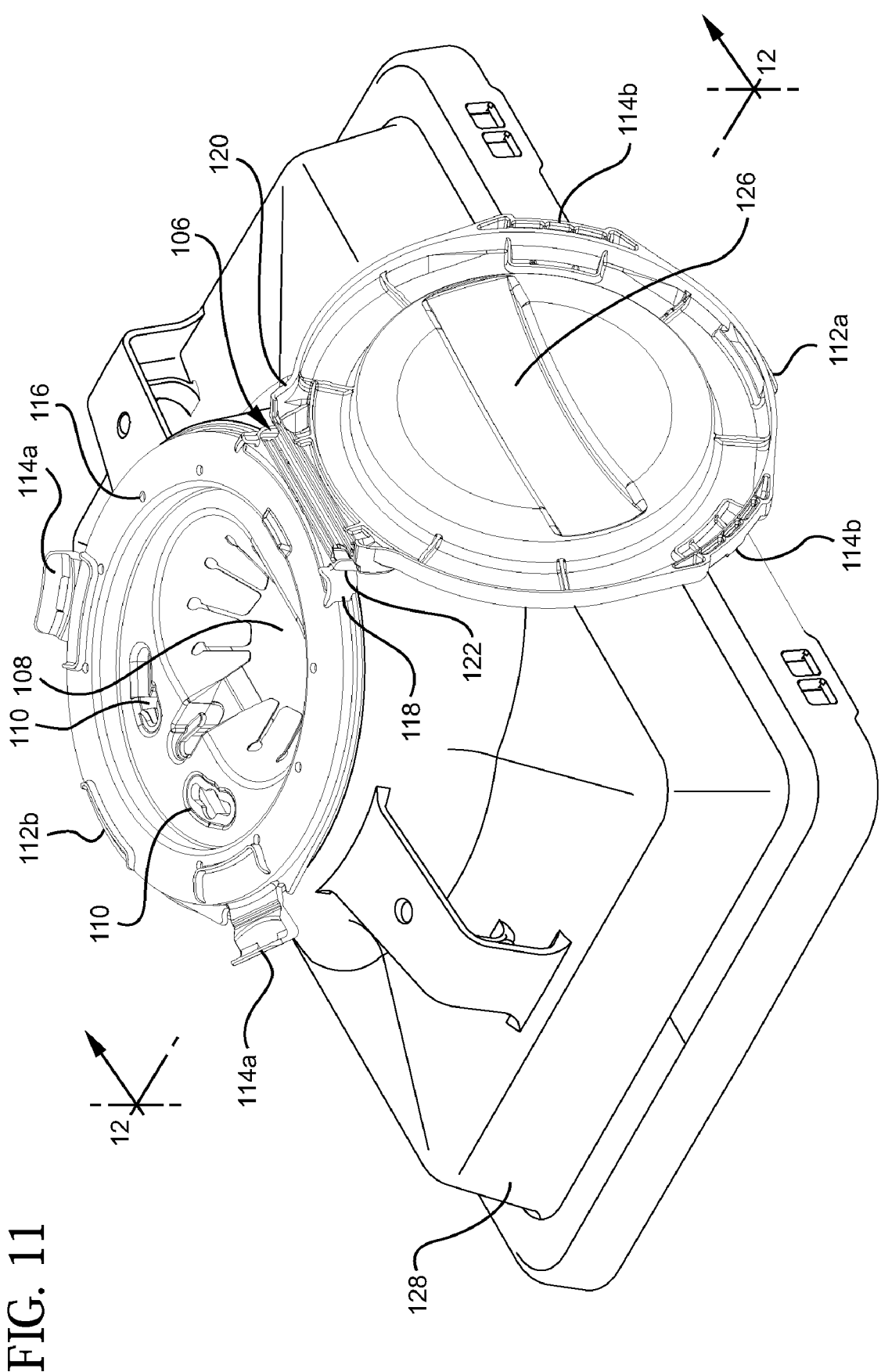
FIG. 11 is a perspective view of a medical waste container lid in an open position on a top container portion, showing the underside of the closure part in the foreground and the top side of the cap part in the background.
Figure 12:
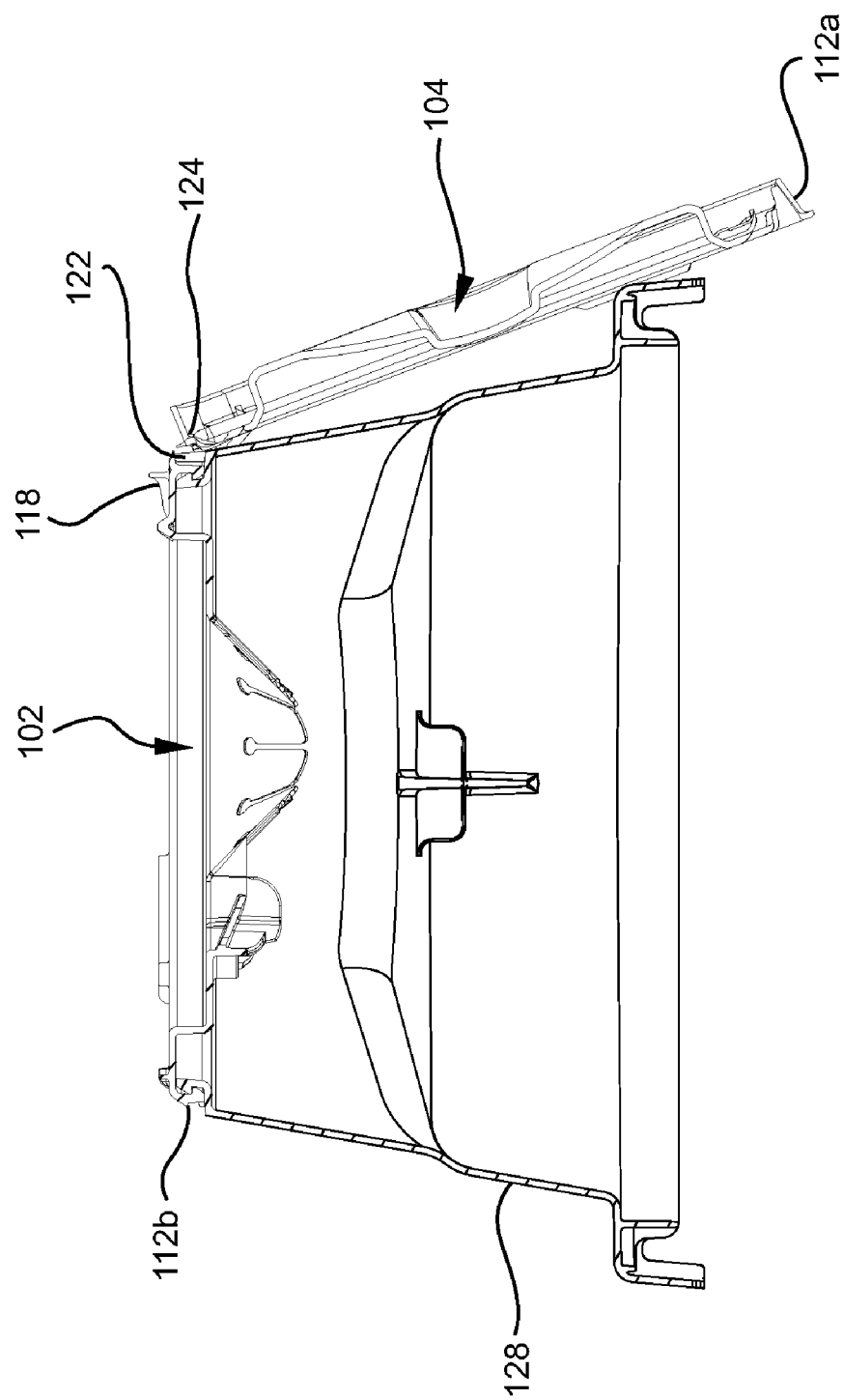
FIG. 12 is a cross section of the container and the medical waste container lid of FIG. 11 taken along line 12-12, showing the closure part on the right side angled downwardly.

The lid according to the second aspect may further include second closure retention structures positioned on either side of the hinge 106. These second closure retention structures are best seen in FIGS. 10-12, and permit the closure part 104 and the cap part 102 to be held in a fixed position in the range of about 180° and 270°. Specifically, the second closure retention structure includes a pair of radially extending projections or fins 122 on opposite sides of the hinge 106 that cooperate with stops 124 shown in the Figures as grooves which engage the projections or fins 122 when the closure part 104 is in a position, relative to the cap part 102, in the range of about 180° and 270°. Application of upward pressure to the closure part 104 will disengage the stops 124 from the fins or projections 122, and the closure part 104 can be rotatably moved about the hinge 106 to close the closure part 104 over aperture 108. It will be appreciated that the configuration of the projections or fins 122 and stops 124 are exemplary only, and other configurations could be used to achieve the result of maintaining the lid in an open position in the range of about 180° and 270°. For example, any suitable projection 122 cooperating with an edge portion projecting from the rear of the closure part 104 that permits the lid to be opened in the desired angular configuration could be used as alternative structures. This second closure retention structure that permits the lid to be opened at angles in the range of about 180° and 270° is useful when the waste disposal container is used on a table top or counter top. It may be desirable for a waste container lid to incorporate both types of closure retention structures that would permit waste containers including such lids to be used in a variety of locations such as mounted on walls, on carts or on table tops.

It will be appreciated from the description above, that a waste container including a lid is provided that may include one or both of the features of the aspects described above. Thus, a lid may include the temporary and permanent locking features as described with respect to the first aspect. A lid according to a second aspect includes closure retention features that hold the lid in a plurality of open positions. In one or more embodiments, these two aspects may be combined in a third aspect to include a lid that has temporary and permanent closure features as described above and closure retention features that hold the lid in a plurality of open positions.

The lid according to each aspect described above may contain a number of optional features. Thus, lid 100 can include a structural bridge 126 on the closure part 104. The purpose of the structural bridge 126 is to increase the stiffness of the lid 100 and provide structural integrity. This will decrease the likelihood of a leak or spill if the top container portion 128 with the lid 100 is dropped or has other items stacked thereon. The structural bridge 126 is an ideal location to apply a logo 130 such as a company logo, or other identifying indicia. In specific embodiments there are two or more permanent locking structures. In some of these embodiments, the two permanent locking structures are positioned on opposite sides of the releasable lock structure.

Other optional features includes a plurality of downwardly facing flexible fingers or petals 131 in the aperture 108, which prevent individuals from removing materials from the container. As will readily be appreciated, if a user reaches through aperture 108 with fingers or petals 131 pointing inwardly and downwardly, the fingers or petals 131 will catch individuals hand and make it difficult to remove an item from the container.

Another optional feature is to configure the size and shape of the closure part and cap part such that the top includes an outwardly curved rim and the cap part of the lid includes a rim around its periphery, the rim of the top container portion and the rim of the cap part are configured to engage each other in an interference fit for connecting the top container portion and the lid. Alternatively, the lid can be held to the top in a snap-fit arrangement achieved by a plurality of inwardly directed projections on the rim of the cap part engaging the rim of the top.

In yet another optional and desirable feature, the closure part 104 and cap part 102 of the lid are sized and shaped complementarily to form a leak resistant seal 145 (shown in FIG. 18) when the lid is in the closed position. The leak resistant seal 145 is adapted to prevent fluids from exiting the container without obstructing optional autoclave vents 116 which are present in one or more embodiments of the invention.

The container and the lid of one or more embodiments are molded from a thermoplastic material. In detailed embodiments, the top and base are separate parts which can be attached.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A waste container comprising:
    a base having a bottom wall, a side wall and a top defining a receptacle for receiving sharps, the side wall extending upwardly from the bottom wall, the top connected to an upper portion of the side wall and having an opening therethrough;
    a lid having a closure part and a cap part having an aperture therethrough, the lid being connectable to the top via the cap part, the lid having a hinge connecting the closure part to the cap part, the hinge allowing the closure part to move between an open position which allows access to the aperture for placing sharps in the receptacle to a closed position covering the aperture;
    a releasable lock structure including a releasable lock detent on one of the cap part or closure part of the lid and a releasable lock projection on the other of the cap part or closure part of the lid, the releasable lock projection adapted to form a connection with the releasable lock detent upon movement of the lid to the closed position, the connection being releasable upon application of force to the releasable lock tab in a direction substantially radial to the lid and allowing the lid to be moved to the open position; and
    at least one permanent lock structure including a permanent lock tab on one of the closure part or the cap part of the lid and a permanent lock catch on the other of the closure part or the cap part of the lid, the permanent lock tab movable to engage the permanent lock catch when the lid is in the closed position, the permanent lock catch adapted to irreversibly engage the permanent lock tab such that force required to open the permanent lock structure is substantially transverse to the force required to move the closed lid to the open position.

2. The waste container of claim 1, further comprising a skirt portion positioned around a periphery of the closure part of the lid, the skirt portion having two opposed edges substantially aligned with two ramps located on the cap part of the lid with the opposed edges of the skirt portion and disposed on opposite sides of the hinge, the edge portions are adapted to cooperate with the ramps to retain the lid in an open position.

3. The waste container of claim 2, wherein the ramps curve radially inwardly toward the hinge and are inclined upwardly towards the hinge.

4. The waste container of claim 3, wherein the edge portions of the skirt are forced apart by interaction with the angled ramps upon closure of the lid, the skirt closing as the edge portions move along the ramps.

5. The waste container of claim 2, wherein the cap part includes radially projecting fins and the closure part includes stops adapted to cooperate with the radially projecting fins to hold the closure part in a fixed position relative to the cap part of the lid.

6. The waste container of claim 2, wherein, the edge portions are adapted to cooperate with the ramps so that the closure part of the lid is held relative to the cap part of the lid in a position between 75° and 135°.

7. The waste container of claim 5, wherein the radially projecting fins and the stops are adapted to cooperate so that the closure part and the cap part of the lid are held in a fixed position between 180° and 270°.

8. The waste container of claim 1, wherein the releasable lock detent is located on the cap part of the lid and the releasable lock projection is located on the closure part of the lid.

9. The waste container of claim 1, wherein the at least one permanent lock structure has the permanent lock catch located on the closure part of the lid and the permanent lock tab located on the cap part of the lid.

10. The waste container of claim 1, wherein the at least one permanent locking structure comprises two permanent locking structures.

11. The waste container of claim 10, wherein the two permanent locking structures are positioned on opposite sides of the releasable lock structure.

12. The waste container of claim 1, wherein the aperture includes a plurality of downwardly facing flexible fingers for helping to keep sharps in the receptacle.

13. The waste container of claim 1, wherein the cap part of the lid includes at least one elongate port for needle removal, the at least one port being covered by the closure part of the lid when the lid is in the closed position.

14. The waste container of claim 1, wherein an upper portion of the top includes an outwardly curved rim and the cap part of the lid includes a rim around its periphery, the rim of the top and the rim of the cap part are configured to engage each other in an interference fit for connecting the top and the lid.

15. The waste container of claim 14, wherein the lid is held to the top in a snap-fit arrangement achieved by a plurality of inwardly directed projections on the rim of the cap part engaging the rim of the top.

16. The waste container of claim 1, wherein the closure part and cap part of the lid form a leak resistant seal when the lid is in the closed position.

17. The waste container of claim 1, further comprising autoclave vents on the cap part of the lid.

18. The waste container of claim 1, wherein the closure part of the lid further comprises a structural bridge for increasing stiffness of the closure part.

19. The waste container of claim 1, wherein the receptacle and the lid are molded from a thermoplastic material.

20. The waste container of claim 1, wherein the top and base are separate attachable parts.

21. A waste container comprising:
a base having a bottom wall, a side wall and a top defining a receptacle for receiving sharps, the side wall extending upwardly from the bottom wall, the top connectable to an upper portion of the side wall and having an opening having an outwardly curved rim;
a lid having a closure part and a cap part, the cap part including a rim configured to engage the rim of the receptacle in an interference fit for sealing the lid to the top of the receptacle, the lid having a hinge connecting the closure part to the cap part, the hinge allowing the closure part to move to and from an open position which allows access to the aperture for placing sharps in the receptacle and a closed position covering the aperture and forming a leak resistant seal, the cap part having an aperture therethrough;
two first closure retention structures positioned on either side of the hinge on the lid, the first closure retention structures having first projection on the cap part and a skirt portion having opposing edges on the closure part, the first projection being curved inwardly towards the hinge and increasing in height along the curve, the opposing edges of the skirt portion adapted to move along the first projection throughout the movement of the lid from a closed position to an open position, the first closure retention structures adapted to hold the closure part of the lid in a position between about 75° and about 135° relative to the cap part of the lid;
two second closure retention structures positioned on either side of the hinge on the lid, the second closure retention structures having projections on the cap part extending radially from the cap part and stops on the closure part of the lid, the stops aligned to interact with the projections on the cap part to hold the closure part of the lid in a position between about 180° and about 270° relative to the cap part of the lid;
a releasable lock structure; and
a permanent locking structure.

22. The waste container of claim 21, wherein the cap part further comprises a plurality of autoclave vents located around the aperture.

23. The waste container of claim 21, wherein the cap part further comprises at least one elongate port for needle removal located adjacent the aperture such that removed needles drop into the receptacle.

24. The waste container of claim 21, wherein the closure part further comprises a structural bridge for increasing stiffness of the closure part.

25. The waste container of claim 21, wherein the releasable lock structure includes a releasable lock detent on the cap part of the lid and a releasable lock projection on the closure part of the lid, the releasable lock projection adapted to fit into a recess in the releasable lock detent when the lid is in the closed position, the connection being releasable upon application of force in a direction substantially radial to the lid and allowing the lid to be moved to the open position 26. The waste container of claim 21, wherein the permanent lock structure includes a permanent lock tab on one of the cap part of the lid or closure part of the lid and a permanent lock catch on the other of the cap part of the lid or the closure part of the lid.

27. The waste container of claim 26 wherein the permanent lock tab has a recess and is movable to engage a projection on the permanent lock catch when the lid is in the closed position, the permanent lock catch adapted to irreversibly engage the permanent lock tab such that the force required to open the permanent locking structure must be applied transversely to the direction that the lid opens.

28. A container closure comprising:
a lid having a closure part and a cap part having an aperture therethrough, the lid being connectable to a container via the cap part, the lid having a hinge connecting the closure part to the cap part, the hinge allowing the closure part to move between an open position which allows access to the aperture for placing sharps in the receptacle to a closed position covering the aperture;
a releasable lock structure including a releasable lock detent on one of the cap part or closure part of the lid and a releasable lock projection on the other of the cap part or closure part of the lid, the releasable lock projection adapted to form a connection with the releasable lock detent upon movement of the lid to the closed position, the connection being releasable upon application of force to the releasable lock tab in a direction substantially radial to the lid and allowing the lid to be moved to the open position; and
at least one permanent lock structure including a permanent lock tab on one of the closure part or the cap part of the lid and a permanent lock catch on the other of the closure part or the cap part of the lid, the permanent lock tab movable to engage the permanent lock catch when the lid is in the closed position, the permanent lock catch adapted to irreversibly engage the permanent lock tab such that force required to open the permanent lock structure is substantially transverse to the force required to move the closed lid to the open position.

* * * * *